United States Patent
Lee et al.

(10) Patent No.: US 9,902,767 B2
(45) Date of Patent: Feb. 27, 2018

(54) METHOD OF BLOCKING VASCULAR LEAKAGE USING AN ANTI-ANG2 ANTIBODY

(71) Applicant: Samsung Electronics Co., Ltd., Suwon-si, Gyeonggi-do (KR)

(72) Inventors: Hyo Seon Lee, Hwaseong-si (KR); Kyung Eun Kim, Yongin-si (KR); Seung Ja Oh, Seoul (KR); Sang Yeul Han, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 50 days.

(21) Appl. No.: 14/446,256

(22) Filed: Jul. 29, 2014

(65) Prior Publication Data

US 2015/0030604 A1 Jan. 29, 2015

(30) Foreign Application Priority Data

Jul. 29, 2013 (KR) .......... 10-2013-0089281
Sep. 5, 2013 (KR) .......... 10-2013-0106749

(51) Int. Cl.
*A61K 39/395* (2006.01)
*C07K 16/22* (2006.01)
*A61K 38/18* (2006.01)
*G01N 33/74* (2006.01)
*A61K 39/00* (2006.01)

(52) U.S. Cl.
CPC .......... *C07K 16/22* (2013.01); *A61K 38/1891* (2013.01); *A61K 39/3955* (2013.01); *G01N 33/74* (2013.01); *A61K 2039/505* (2013.01); *C07K 2316/96* (2013.01); *C07K 2317/34* (2013.01); *C07K 2317/55* (2013.01); *C07K 2317/565* (2013.01); *C07K 2317/74* (2013.01); *C07K 2317/75* (2013.01); *C07K 2317/76* (2013.01); *C07K 2317/77* (2013.01); *C07K 2317/92* (2013.01); *G01N 2333/515* (2013.01); *G01N 2333/71* (2013.01); *G01N 2500/02* (2013.01)

(58) Field of Classification Search
None
See application file for complete search history.

(56) References Cited

U.S. PATENT DOCUMENTS

| 5,567,440 | A | * | 10/1996 | Hubbell | A61K 9/5031 424/484 |
| 5,859,205 | A | * | 1/1999 | Adair | C07K 16/18 530/387.1 |
| 6,365,154 | B1 | | 4/2002 | Holmes et al. | |
| 6,455,035 | B1 | | 9/2002 | Suri et al. | |
| 7,052,695 | B2 | | 5/2006 | Kalish | |
| 7,081,443 | B2 | | 7/2006 | Koh | |
| 7,309,483 | B2 | | 12/2007 | Wiegand et al. | |
| 8,361,747 | B2 | | 1/2013 | Brinkmann et al. | |
| 8,524,870 | B2 | | 9/2013 | Takayama et al. | |
| 8,685,393 | B2 | * | 4/2014 | Parikh | A61K 38/4866 424/130.1 |
| 8,834,880 | B2 | | 9/2014 | Green et al. | |
| 2004/0023880 | A1 | | 2/2004 | Gale et al. | |
| 2007/0154482 | A1 | | 7/2007 | Sukhatme et al. | |
| 2008/0267971 | A1 | | 10/2008 | Green et al. | |
| 2010/0048900 | A1 | | 2/2010 | Schwarz | |
| 2010/0267615 | A1 | | 10/2010 | Petzelbauer et al. | |
| 2011/0027286 | A1 | | 2/2011 | Thurston et al. | |
| 2011/0044998 | A1 | | 2/2011 | Bedian et al. | |
| 2011/0097300 | A1 | | 4/2011 | Slyke et al. | |
| 2011/0150895 | A1 | | 6/2011 | Ryu et al. | |
| 2011/0268694 | A1 | | 11/2011 | Shalwitz et al. | |
| 2011/0274699 | A1 | | 11/2011 | Rotello et al. | |
| 2012/0052073 | A1 | | 3/2012 | Green et al. | |
| 2012/0128625 | A1 | | 5/2012 | Shalwitz et al. | |
| 2012/0129847 | A1 | | 5/2012 | Peters et al. | |
| 2012/0141499 | A1 | | 6/2012 | Oliner et al. | |
| 2012/0258122 | A1 | | 10/2012 | Boone et al. | |
| 2013/0095065 | A1 | | 4/2013 | Peters et al. | |
| 2013/0129722 | A1 | | 5/2013 | Lowy et al. | |
| 2013/0142799 | A1 | | 6/2013 | Oliner et al. | |
| 2013/0156789 | A1 | | 6/2013 | Brinkmann et al. | |
| 2014/0044723 | A1 | | 2/2014 | Takayama et al. | |
| 2014/0113858 | A1 | * | 4/2014 | Han | C07K 14/515 514/7.6 |

FOREIGN PATENT DOCUMENTS

EP 2848631 A1 3/2015
JP 2002-540165 A 11/2002
(Continued)

OTHER PUBLICATIONS

Thamm and David. Role of angiopoietin-2 in infection—a double-edged sword? Cytokine 83 (2016) 61-63.*
Rittirsch et al. The disconnect between animal models of sepsis and human sepsis. Journal of Leukocyte Biology 81:137-143, 2007.*
Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*
Thurston et al. The Complex Role of Angiopoietin-2 in the Angiopoietin-Tie Signaling Pathway. Cold Spring Harb Perspect Med 2012;2:a006650, pp. 1-13.*

(Continued)

*Primary Examiner* — Maher M Haddad

(74) *Attorney, Agent, or Firm* — Leydig, Voit & Mayer, Ltd.

(57) ABSTRACT

A method for the prevention and/or treatment of a disease accompanied by vascular leakage and/or vascular inflammation comprising administering an anti-Ang2 antibody or an antigen-binding fragment thereof that specifically binds to an angiogenesis-inducing factor Angiopoietin-2 (Ang2) and forms a complex with a Tie2 receptor and Ang2.

13 Claims, 20 Drawing Sheets

(4 of 20 Drawing Sheet(s) Filed in Color)

(56) References Cited

FOREIGN PATENT DOCUMENTS

| | | |
|---|---|---|
| JP | 2011-105695 A | 2/2011 |
| KR | 1020100005202 A | 1/2010 |
| KR | 1020100118143 A | 11/2010 |
| WO | 00/57901 A1 | 10/2000 |
| WO | WO 2006/045049 A1 | 4/2006 |
| WO | WO 2006/068953 A2 | 6/2006 |
| WO | WO 2006/118350 A1 | 11/2006 |

OTHER PUBLICATIONS

Pfetsch et al. Protective effect of angiopoietin-2 antibodies in a murine model of LPS-induced sepsis. Journal of Vascular Research, (Sep. 2011) vol. 48, Supp. Suppl. 1, pp. 281. Abstract No. P 170.*
Holopainen et al. Effects of Angiopoietin-2-Blocking Antibody on Endothelial Cell-Cell Junctions and Lung Metastasis. J Natl Cancer Inst 2012;104:461-475.*
Slotta et al. Blockade of Ang-2 reduces endotoxin-induced hepatic microvascular dysfunction. Chirurgisches Forum 2007 vol. 36 of the series Deutsche Gesellschaft für Chirurgie, abstract.*
Zhu et al. Methicillin-resistant *Staphylococcus aureus*-induced vascular hyperpermeability is mediated by nitric oxide and reactive nitrogen species. Free Radical Biology and Medicine, (2009) vol. 47, Suppl 1, pp. S39-S40. Abstract No. 81.*
Paul, Fundamental Immunology, 3rd Edition, 1993, pp. 292-295.*
Tzepi et al. Angiopoietin-2 Enhances Survival in Experimental Sepsis Induced by Multidrug-Resistant Pseudomonas aeruginosa. J. Pharmacol. Exp. Ther. 343 (2012) 278-287.*
Barton et al, Structure of the Angiopoietin-2 Receptor Binding Domain and Identification of Surfaces Involved in Tie2 Recognition. Structure, vol. 13, 825-832, May 2005.*
Brown et al. Tolerance of single, but not multiple, amino acid replacements in antibody VH CDR 2: a means of minimizing B cell wastage from somatic hypermutation? J. Immuno. May 1996, 3285-91.*
Rudikoff et al Single amino acid substitution altering antigen-binding specificity. Proc Natl Acad Sci U S A. Mar. 1982;79(6):1979-83.*
Eduardo Padlan, Anatomy of the antibody molecule. Mol Immunol. Feb. 1994;31(3):169-217.*
Campbell A, General properties and applications of monoclonal antibodies, Elsevier Science Publishers, section 1.1, pp. 1-32, 1984.*
Han et al. Amelioration of sepsis by TIE2 activation-induced vascular protection. Sci Transl Med. Apr. 20, 2016;8(335):335ra55.*
David et al. Angiopoietin-2 may contribute to multiple organ dysfunction and death in sepsis. Crit Care Med. Nov. 2012; 40(11): 3034-3041.*
Fink, M.P., Animal models of sepsis. Virulence 5:1, 143-153; Jan. 1, 2014.*
Van Regenmortel MHV. Mapping Epitope Structure and Activity: From One-Dimensional Prediction to Four-Dimensional Description of Antigenic Specificity Methods. 9(3):465-72, 1996.*
Lerner RA. Tapping the immunological repertoire to produce antibodies of predetermined specificity. Nature 1982; 299:592-596.*
Abcam: "Anti-Angiopoientin 2 antibody ab8452", abcam Online Catalogue, Nov. 13, 2014.
Barton et al., "Crystal structures of the Tie2 receptor ectodomain and the angiopoietin-2-Tie2 complex", *Nature Structural & Molecular Biology*, 13 (6): 524-532 (2006).
Bogdanovic et al., "Activation of Tie2 by angiopoietin-1 and angiopoietin-2 results in their release and receptor internalization", *Journal of Cell Science*, 119 (17): 3551-3560 (2006).
Santa Cruz Biotechnology, inc. : "Ang-2 (F-1): sc-74403", Santa Cruz Biotechnology Online Catalogue, Mar. 22, 2013.
Srirajaskanthan et al., "Circulating angiopoietin-2 is elevated in patients with neuroendocrine tumours and correlates with disease burden and prognosis", *Endocrine-Related Cancer*, 16 (3): 967-976 (2009).

Yao et al., "High glucose increases angiopoientin-2 transcription in microvascular endothelial cells through methylglyoxal modification of mSin3A", *The Journal of Biological Chemistry*, 282(42): 31038-31045 (2007).
Yuan et al., "Angiopoietin 2 Is a Partial Agonist/Antagonist of Tie2 Signaling in the Endothelium", *Molecular and Cellular Biology*, 29(8): 2011-2022 (2009).
Ziegler et al., "Angiopoietin 2 mediates microvascular and hemodynamic alterations in sepsis", *Journal of Clinical Investigation*, 123(8): 3436-3445 (2013).
European Patent Office, Extended European Search Report in Application No. 14178843.0 dated Nov. 27, 2014.
European Patent Office, Extended European Search Report in Application No. 14178844.8 dated Dec. 8, 2014.
Gamble et al., "Angiopoietin-1 is an Antipermeability and Anti-Inflammatory Agent in Vitro and Targets Cell Junctions", *Circulation Research*, 87: 603-607 (2000).
David et al., "Acute administration of recombinant Angiopoietin-1 ameliorates multiple-organ dysfunction syndrome and improves survival in murine sepsis", *Cytokine*, 55: 251-259 (2011).
Parikh et al., "Excess Circulating Angiopoietin-2 May Contribute to Pulmonary Vascular Leak in Sepsis in Humans", *PLoS Medicine*, 3(3), e46 pp. 0356-0379 (2006).
Kümpers et al., "Time course of angiopoietin-2 release during experimental human endotoxemia and sepsis," *Critical Care*, 13: R64, pp. 1-9 (2009).
Kümpers et al., "Excess circulating angiopoietin-2 is a strong predictor of mortality in critically ill medical patients", *Critical Care*, 12: R147, pp. 1-9 (2008).
Gu et al., "Angiopoietin-1/Tie2 signaling pathway inhibits lipopolysaccharide-induced activation of RAW264.7 macrophage cells", *Biochemical and Biophysical Research Communications*, 392, 178-182 (2010).
Hwang et al, "COMP-Ang1 Potentiates the Antitumor Activity of 5-Fluorouracil by Improving Tissue Perfusion in Murine Lewis Lung Carcinoma", *Mol Cancer Res*, 7: 1920-1927 (2009).
Cho et al., "Designed angiopoietin-1 variant, COMP-Ang1, protects against radiation-induced endothelial cell apoptosis", *PNAS*, 10 (15), 5553-5558 (2004).
Kümpers et al., "The synthetic Tie2 agonist peptide vasculotide protects against vascular leakage and reduces mortality in murine abdominal sepsis", *Critical Care*, (15):R261 pp. 1-14 (2011).
David et al, "Effects of a synthetic PEG-ylated Tie-2 agonist peptide on endotoxemic lung injury and mortality", *AM J Physiol Lung Cell Mol Physiol*, 300: L851-L862 (2011).
Jain et al., "Normalization of Tumor Vasculature: An Emerging Concept in Antiangiogenic Therapy", *Science*, 307: 58-62 (2005).
David et al., "Angiopoietin-2 may contribute to multiple organ dysfunction and death in sepsis", *Critical Care Med*, 40(11), 3034-3041 (2012).
Van Regenmortel, M.H.V., "Mapping Epitope Structure and Activity: From One-Dimensional Prediction to Four-Dimensional Description of Antigenic Specificity", *Methods*, 9(3):465-72, 1996.
European Patent Office, Examination Report in European Patent Application No. 14178844.8 dated Mar. 15, 2016, pp. 1-10.
United States Patent & Trademark Office, Office Action in U.S. Appl No. 14/446,228 dated Apr. 22, 2016, pp. 1-25.
Cunningham et al., "High-Resolution Epitope Mapping of hGH-Receptor Interactions by Alanine-Scanning Mutagenesis", *Science*, 244:1081-1085 (1989).
Mai et al., "Experimental Sepsis Models", Intech, Chapter 2, 35-70 (2012).
Popov et al., "Sepsis Models in Experimental Animals", *Trakia Journal of Sciences*, 1:13-23 (2013).
Verma, "Laboratory Animal Models to Mimic Human Sepsis: A Review", Research & Reviews: Journal of Zoological Sciences, (4)2: 34-39 (Jan.-Jun. 2016).
Shotgun Mutagenesis leaflet from Integral Molecular (2012).
European Patent Office, Office Action in European Patent Application No. 14178844.8 dated Sep. 5, 2016, pp. 1-11.
Chang et al., The role of angiopoietin-2 in progressive renal fibrosis, *Journal of the Formosan Medical Association*,112: 175-176 (2013).

(56) References Cited

OTHER PUBLICATIONS

Kloepper et al., Ang-2/VEGF bispecific antibody reprograms macrophages and resident microglia to anti-tumor phenotype and prolongs glioblastoma survival, PNAS, 113(16): 4476-4481 (2016).
Metheny-Barlow et al., The enigmatic role of angiopoletin-1 in tumor angiogenesis, *Cell Research*, 13(5): 309-317 (2003).
Simcock et al., Proangiogenic Activity in Bronchoalveolar Lavage Fluid from Patients with Asthma, *American Journal of Respiratory and Critical Care Medicine*, 176: 146-153 (2007).
Yuan et al., Angiopoietin 2 is a Partial Agonist/Antagonist of Tie2 Signaling in the Endothelium, *Molecular and Cellular Biology*, 29(8): 2011-2022 (2009).
European Patent Office, Office Action in European Patent Application No. 14178844.8 dated Feb. 8, 2017, pp. 1-6.
Leow, et al., "MEDI3617, a human anti-Angiopoietin 2 monoclonal antibody, inhibits angiogenesis and tumor growth in human tumor xenograft models," *International Journal of Oncology*, 40, 1321-1330 (2012).

\* cited by examiner

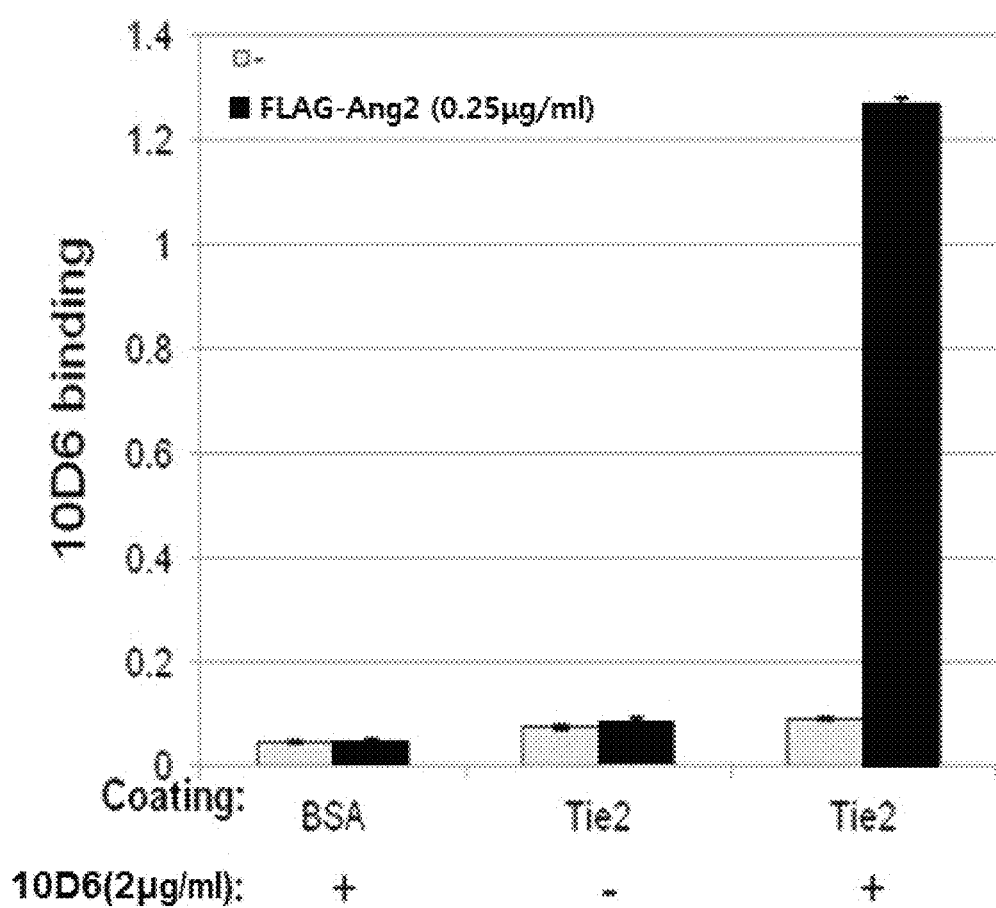

FIG. 5
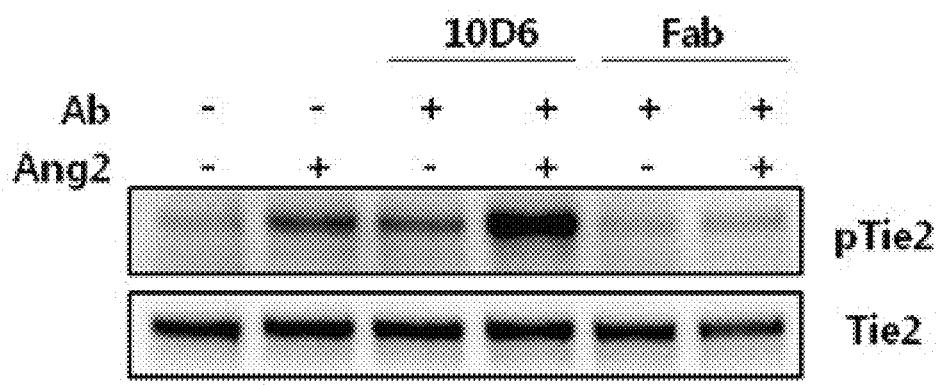
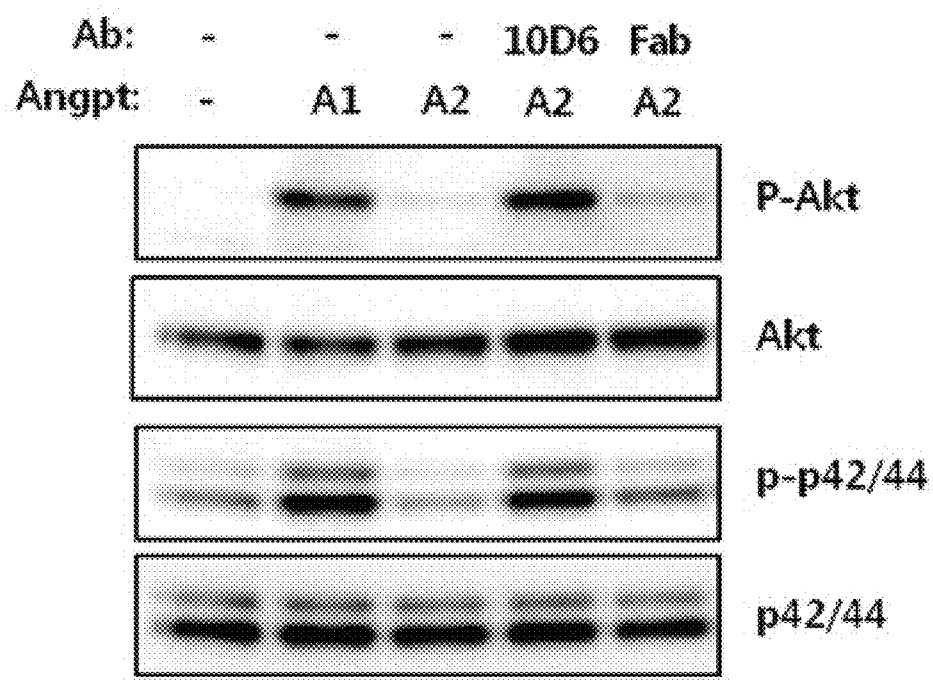

FIG. 7
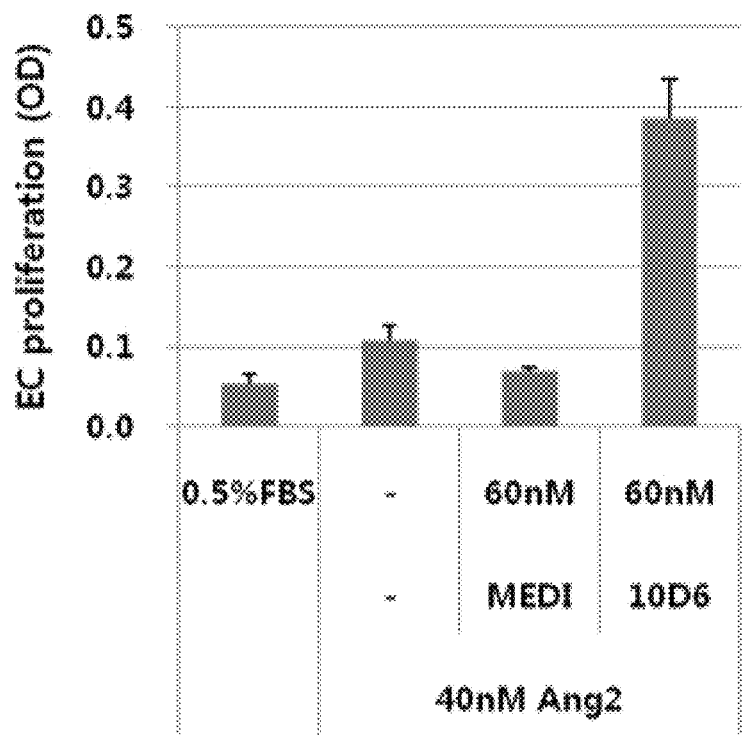
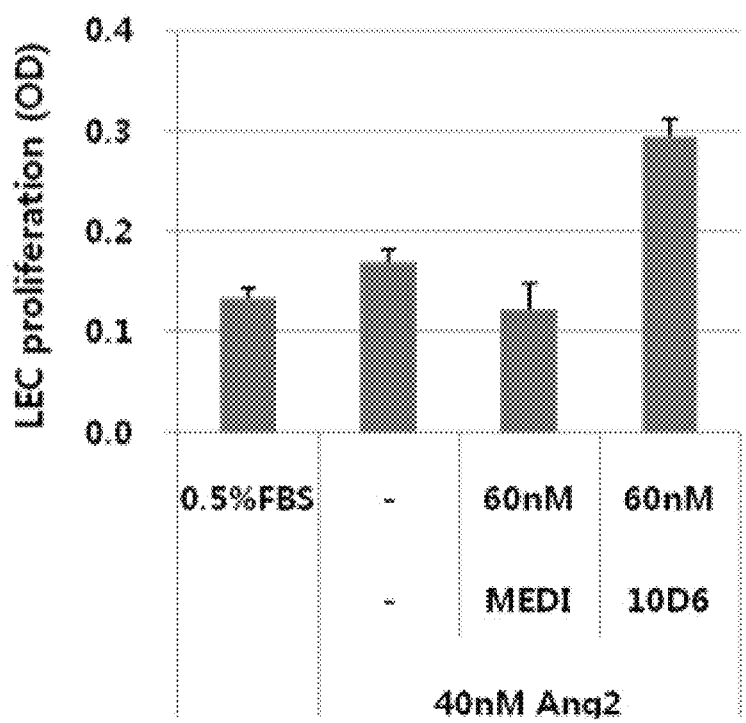

* Indicates P <0.01

```
                        SEQUENCE LISTING

<160> NUMBER OF SEQ ID NOS: 13

<210> SEQ ID NO 1
<211> LENGTH: 6
<212> TYPE: PRT
<213> ORGANISM: Artificial Sequence
<220> FEATURE:
<223> OTHER INFORMATION: Synthetic (CDR-H1 of anti-Ang2 antibody)

<400> SEQUENCE: 1

Ser Asp Tyr Ala Trp Asn
1               5

<210> SEQ ID NO 2
<211> LENGTH: 16
<212> TYPE: PRT
<213> ORGANISM: Artificial Sequence
<220> FEATURE:
<223> OTHER INFORMATION: Synthetic (CDR-H2 of anti-Ang2 antibody)

<400> SEQUENCE: 2

Tyr Ile Asn Tyr Ser Gly Asn Thr Asp Tyr Asn Pro Ser Leu Lys Ser
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Synthetic (CDR-H3 of anti-Ang2 antibody)

<400> SEQUENCE: 3

Gly Asn Phe Glu Gly Ala Met Asp Tyr
1               5
```

<210> SEQ ID NO 4
<211> LENGTH: 11
<212> TYPE: PRT
<213> ORGANISM: Artificial Sequence
<220> FEATURE:
<223> OTHER INFORMATION: Synthetic (CDR-L1 of anti-Ang2 antibody)

<400> SEQUENCE: 4

Lys Ala Ser Gln Ser Val Ser Asn Asp Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic (CDR-L2 of anti-Ang2 antibody)

<400> SEQUENCE: 5

Tyr Ala Ser Asn Arg Tyr Pro
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic (CDR-L3 of anti-Ang2 antibody)

<400> SEQUENCE: 6

Gln Gln Asp Tyr Ser Ser Pro Trp Thr
1               5

<210> SEQ ID NO 7
<211> LENGTH: 118
<212> TYPE: PRT
<213> ORGANISM: Artificial Sequence
<220> FEATURE:
<223> OTHER INFORMATION: Synthetic (Heavy chain variable region of an
      anti-Ang2 antibody)

<400> SEQUENCE: 7

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Asn Tyr Ser Gly Asn Thr Asp Tyr Asn Pro Ser Leu
    50                  55                  60

Lys Ser Arg Ser Ser Ile Thr Arg Asp Thr Ser Lys Asn Gln Phe Phe
65                  70                  75                  80

Leu Gln Leu Asn Ser Val Thr Thr Gly Asp Thr Ala Thr Tyr Tyr Cys
                85                  90                  95

Ala Arg Gly Asn Phe Glu Gly Ala Met Asp Tyr Trp Gly Gln Gly Thr
            100                 105                 110

Ser Val Thr Val Ser Ser
        115

<210> SEQ ID NO 8
<211> LENGTH: 354
<212> TYPE: DNA
<213> ORGANISM: Artificial Sequence
<220> FEATURE:

<223> OTHER INFORMATION: Synthetic (Coding DNA of heavy chain variable
      region of anti-Ang2 antibody)

<400> SEQUENCE: 8
gatgtgcagc ttcaggagtc gggacctgac ctggtgaaac cttctcagtc tctgtccctc    60
acctgcactg tcactggcta ctcaatcacc agtgattatg cctggaactg gatccggcag   120
tttccaggaa acaaactgga gtggatgggc tacataaact acagtggtaa cactgactac   180
aacccatctc tcaaaagtcg aagctctatc actcgagaca catccaagaa ccagttcttc   240
ctgcagttga attctgtgac tactggggac acagccacat attactgtgc aagaggtaac   300
ttcgaaggtg ctatggacta ctggggtcaa ggaacctcag tcaccgtctc ctca          354

<210> SEQ ID NO 9
<211> LENGTH: 107
<212> TYPE: PRT
<213> ORGANISM: Artificial Sequence
<220> FEATURE:
<223> OTHER INFORMATION: Synthetic (Light chain variable region of
      anti-Ang2 antibody)

<400> SEQUENCE: 9

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Pro Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Trp
                85                  90                  95

Thr Phe Gly Gly Gly Thr Lys Leu Glu Ile Lys
            100                 105

<210> SEQ ID NO 10
<211> LENGTH: 321
<212> TYPE: DNA
<213> ORGANISM: Artificial Sequence
<220> FEATURE:
<223> OTHER INFORMATION: Synthetic (Coding DNA of light chain variable
      region of anti-Ang2 antibody)

<400> SEQUENCE: 10
agtattgtga tgacccagac tcccaaattc ctgcttgtat cagcaggaga cagggttacc    60
ataacctgca aggccagtca gagtgtgagt aatgatgtag cttggtacca acagaagcca   120
gggcagtctc ctaaactgct gatatactat gcatccaatc gctacctgg agtccctgat    180 cgcttcactg gcagtggata tgggacggat ttcactttca ccatcagcac tgtgcaggct   240
gaagacctgg cagtttattt ctgtcagcag gattatagct ctccgtggac gttcggtgga   300
ggcaccaagc tggaaatcaa a                                              321

<210> SEQ ID NO 11
<211> LENGTH: 496
<212> TYPE: PRT
<213> ORGANISM: Artificial Sequence
<220> FEATURE:
<223> OTHER INFORMATION: Synthetic (amino acid sequence of Ang2)

<400> SEQUENCE: 11

```
Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
                85                  90                  95

Leu Glu Asn Tyr Ile Gln Asp Asn Met Lys Lys Glu Met Val Glu Ile
                100                 105                 110

Gln Gln Asn Ala Val Gln Asn Gln Thr Ala Val Met Ile Glu Ile Gly
            115                 120                 125

Thr Asn Leu Leu Asn Gln Thr Ala Glu Gln Thr Arg Lys Leu Thr Asp
130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
                180                 185                 190

Lys Lys Val Leu Ala Met Glu Asp Lys His Ile Ile Gln Leu Gln Ser
            195                 200                 205

Ile Lys Glu Glu Lys Asp Gln Leu Gln Val Leu Val Ser Lys Gln Asn
210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
                260                 265                 270

Val Ala Lys Glu Glu Gln Ile Ser Phe Arg Asp Cys Ala Glu Val Phe
            275                 280                 285

Lys Ser Gly His Thr Thr Asn Gly Ile Tyr Thr Leu Thr Phe Pro Asn
290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
355                 360                 365

Tyr Val Leu Lys Ile His Leu Lys Asp Trp Glu Gly Asn Glu Ala Tyr
            370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
```

```
                        405                 410                 415
Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
            435                 440                 445

Ala Cys Gly Pro Ser Asn Leu Asn Gly Met Tyr Tyr Pro Gln Arg Gln
            450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 12
<211> LENGTH: 121
<212> TYPE: PRT
<213> ORGANISM: Artificial Sequence
<220> FEATURE:
<223> OTHER INFORMATION: Synthetic (heavy chain variable region of 4H10)

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Leu Ile Ser Pro Asp Ser Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Ile Ser Phe Trp Arg Gly Gly Phe Asp Tyr Trp Gly
            100                 105                 110

Gln Gly Thr Leu Val Thr Val Ser Ser
        115                 120

<210> SEQ ID NO 13
<211> LENGTH: 111
<212> TYPE: PRT
<213> ORGANISM: Artificial Sequence
<220> FEATURE:
<223> OTHER INFORMATION: Synthetic (light chain variable region of 4H10)

<400> SEQUENCE: 13

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Tyr Val Asn Trp Tyr Gln Gln Leu Pro Gly Thr Ala Pro Lys Leu Leu
        35                  40                  45

Ile Tyr Ala Asp Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80
```

```
Ser Glu Asp Glu Ala Asp Tyr Tyr Cys Gly Ser Trp Asp Tyr Ser Leu
                85                  90                  95

Ser Gly Tyr Val Phe Gly Gly Gly Thr Lys Leu Thr Val Leu Gly
            100                 105                 110
```

METHOD OF BLOCKING VASCULAR LEAKAGE USING AN ANTI-ANG2 ANTIBODY

CROSS-REFERENCE TO RELATED APPLICATIONS

This application claims the benefit of Korean Patent Application Nos. 10-2013-0089281 filed on Jul. 29, 2013 and 10-2013-0106749 filed on Sep. 5, 2013 in the Korean Intellectual Property Office, the entire disclosures of which are hereby incorporated by reference.

INCORPORATION BY REFERENCE OF ELECTRONICALLY SUBMITTED MATERIALS

Incorporated by reference in its entirety herein is a computer-readable nucleotide/amino acid sequence listing submitted herewith and identified as follows: 11,824 bytes ASCII (Text) file named "717997_ST25.TXT," created Jul. 29, 2014.

BACKGROUND

1. Field

Provided is an anti-Ang2 antibody or an antigen-binding fragment thereof that specifically binds to an angiogenesis-inducing factor Angiopoietin-2 (Ang2) and complexes with a Tie2 receptor when bound to Ang2, and a use for prevention and/or treatment of a disease accompanied by vascular leakage and/or vascular inflammation.

2. Description of the Related Art

Angiopoietin-2 (Ang2) is an antagonistic ligand of a receptor Tie2 present at vascular endothelial cells. It is believed to suppress signaling by Tie2 by competing with Angiopoietin-1 (Ang1), which is an agonist of Tie2, to bind to Tie2. Ang1, which is a ligand activating the Tie2 receptor, functions as a key regulator of maintaining the stabilization of blood vessels by maintaining the barrier function of vascular endothelial cells. The vascular endothelial cells are activated, demonstrated by the overexpression of VEGF or inflammation, and vascular permeability is increased. It is thought that Ang1 induces the stabilization of vascular endothelial cells and reduces vascular permeability by accelerating the junctional integrity of the vascular endothelial cells whereas Ang2 which is increased in the activated vascular endothelial cells serves to suppress the stabilization of the vascular endothelial cells by Ang1 by competing with Ang1. Therefore, Ang2 inhibits Ang1-Tie2 binding which maintains the stability of the vascular endothelial cells and signaling thereby, thus ultimately accelerating angiogenesis via the dynamic rearrangement of blood vessels.

As angiogenesis is an important element for the growth of cancer, preventing the additional growth of cancer by inhibiting the function of Tie2-dependent Ang2 to suppress angiogenesis has been known by the research of several preclinical models and in fact, various attempts to prevent the progress of cancer using anti-Ang2 antibodies are ongoing.

The overexpression of Ang2 in a variety of solid cancers and blood cancers has been reported, and Ang2 expression in a serum often serves as a biomarker of poor prognosis. The overexpression of Ang2 has been reported not only in the cancers but also in various diseases including sepsis, bacterial infection, lung injury and kidney injury, and of them, its correlation with vascular leakage has been vigorously studied. Due to the correlation with such pathological conditions, Ang2 has been considered to be an important target in therapeutic intervention. Currently, a variety of drugs being developed are in their clinical or preclinical stages, and they have a variety of forms including a peptibody, bispecific antibody, monoclonal antibody, etc.

However, most of the Ang2-target drugs have mechanisms of suppressing the activation of a Tie2 receptor and its downstream signaling by inhibiting Ang2 from binding to the Tie2 receptor. Therefore, the pre-existing Ang2-target drugs cannot be expected to perform vascular normalization by Tie2 receptor and its downstream signaling.

SUMMARY

One embodiment provides an anti-Ang2 antibody or an antigen-binding fragment thereof, that specifically binds to an angiogenesis-inducing factor Ang2 (Angiopoietin-2) and complexes with a Tie2 receptor when bound to Ang2 to induce the activation of the Tie2 receptor.

Another embodiment provides a hybridoma cell line producing a monoclonal antibody of the anti-Ang2 antibody.

Another embodiment provides an anti-Ang2 antibody-Ang2 complex (e.g., a conjugate) wherein the anti-Ang2 antibody or an antigen-binding fragment thereof and Ang2 are bound to each other.

Another embodiment provides a method for decreasing vascular permeability comprising administering the anti-Ang2 antibody or an antigen-binding fragment thereof to a subject.

Another embodiment provides a method of activating Tie2 receptor including administrating the anti-Ang2 antibody or an antigen-binding fragment thereof to a subject.

Another embodiment provides a method of inhibiting angiogenesis including administering the anti-Ang2 antibody or an antigen-binding fragment thereof to a subject.

Another embodiment provides a pharmaceutical composition including the anti-Ang2 antibody or an antigen-binding fragment thereof as an active ingredient.

Another embodiment provides a method of inhibiting angiogenesis including administering the anti-Ang2 antibody or an antigen-binding fragment thereof to a subject.

Another embodiment provides a method of decreasing vascular permeability including administering the anti-Ang2 antibody or an antigen-binding fragment thereof to a subject.

Another embodiment provides a method of blocking vascular leakage including administering the anti-Ang2 antibody or an antigen-binding fragment thereof to a subject.

Another embodiment provides a method of inducing normal blood vessel formation including administering the anti-Ang2 antibody or an antigen-binding fragment thereof to a subject.

Another embodiment provides a method of preventing and/or treating a disease related to angiogenesis, increase of vascular permeability, and/or decrease of normal blood vessel formation, including administering the anti-Ang2 antibody or an antigen-binding fragment thereof to a subject.

Another embodiment provides a method of preventing and/or treating a disease accompanied by vascular leakage, including administering the anti-Ang2 antibody or an antigen-binding fragment thereof to a subject.

Another embodiment provides a method of preventing and/or treating a disease accompanied by vascular inflammation, including administering the anti-Ang2 antibody or an antigen-binding fragment thereof to a subject.

Another embodiment provides a method of preventing and/or treating sepsis, including administering the anti-Ang2 antibody or an antigen-binding fragment thereof to a subject.

Another embodiment provides a method of inhibiting Ang2 and/or activating a Tie2 receptor including administering the anti-Ang2 antibody or an antigen-binding fragment thereof to a subject.

Another embodiment provides a method of diagnosing a disease related to overexpression of Ang2.

Another embodiment provides a complex in which the anti-Ang2 antibody and the antigen-binding fragment thereof, Ang2, and a Tie2 receptor are bound to one another (e.g., the anti-Ang2 antibody and the antigen-binding fragment thereof specifically binds to Ang2, and the Ang2 binds to a Tie2 receptor).

Still another embodiment provides a method of activating Tie2 receptor including administering the complex in which the anti-Ang2 antibody and the antigen-binding fragment thereof, Ang2, and a Tie2 receptor are bound to one another (e.g., the anti-Ang2 antibody and the antigen-binding fragment thereof specifically binds to Ang2, and the Ang2 binds to a Tie2 receptor), to a subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 is a graph showing the ELISA results showing the formation of a complex by the binding of an anti-Ang2 antibody with Ang2 and Tie2.

FIG. 5 is an annotated photograph of the immunoblotting results showing the phosphorylation of a Tie2 receptor of a monomeric anti-Ang2 antibody and proteins involved in the downstream signaling of the Tie2 receptor.

FIG. 7 is a graph showing the proliferation of vascular and lymphatic endothelial cells when treated with an anti-Ang2 antibody.

DETAILED DESCRIPTION

Figure 1:
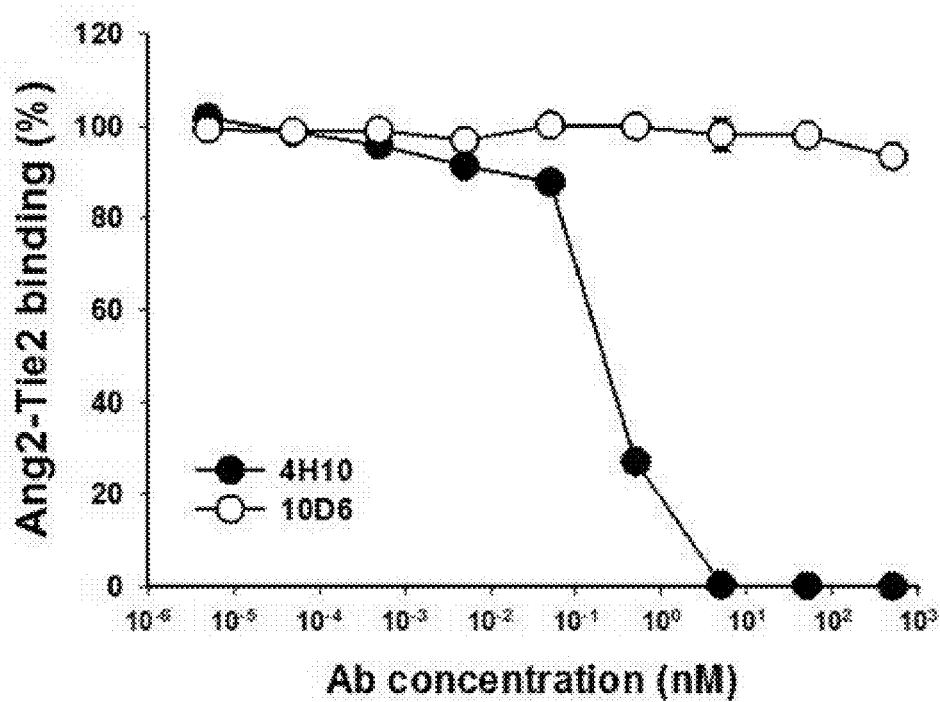
FIG. 1 is a graph of the Ang2-Tie2 competition ELISA results showing the suppression of binding between Tie2 receptor and Ang2 according to the treatment concentration of an anti-Ang2 antibody.

The inventors have verified that an antibody which specifically binds to Ang2 but does not inhibit binding between Ang2 and a Tie2 receptor and forms a complex (antibody/Ang2/Tie2) together with Ang2 and the Tie2 receptor has a characteristic of inducing the dimerization of the antibody. Through this, it can induce the activation of the Tie2 receptor and its downstream signaling by effectively clustering the Tie2 receptor in the complex. The antibody having such a mechanism of action inhibits Ang2 functions by binding to Ang2 to induce the intracellular internalization and degradation thereof and thus lowers the level of circulating Ang2. At the same time, it induces Tie2 downstream signaling by binding to a Tie2 receptor together with (via) Ang2 to activate the Tie2 receptor, like Ang1 and induces the stabilization of vascular endothelial cells, thereby having dual functions.

Provided is a therapeutic antibody targeting an angiogenesis-inducing factor Ang2 and particularly, to an anti-Ang2 antibody which not only inhibits the functions of Ang2 by specifically binding to Ang2 thereby inhibiting angiogenesis and decreasing density of blood vessels in tumor tissue but also induces the activation of Tie2 by allowing Ang2 to bind Tie2 thereby structurally and/or functionally normalizing the blood vessels. The anti-Ang2 antibody may bind Ang2 in such a way that Ang2 may still bind with Tie2. The anti-Ang2 antibody may not directly bind to Tie2 receptor, but it can form a complex with Tie2 by binding Ang2 which, in turn, binds Tie2 receptor. The anti-Ang2 antibody has the effects of treating diseases by binding to a Tie2 receptor together with Ang2 to activate the Tie2 receptor and thus induce the structural/functional normalization of blood vessels, along with the down-regulation of Ang2 in diseases related to the dysfunction (e.g., vascular leakage) and the abnormal activation of blood vessels such as cancer, sepsis, eye disorders, etc.

One embodiment provides an anti-Ang2 antibody or an antigen-binding fragment thereof, specifically binding to (recognizing) an angiogenesis-inducing factor Ang2 (Angiopoietin-2) and binding to a Tie2 receptor together with Ang2 (e.g., via Ang2). Thus, the anti-Ang2 antibody or an antigen-binding fragment thereof may specifically recognize and/or bind to Ang2 and bind to Tie2 receptor via Ang2. Also, the anti-Ang2 antibody or an antigen-binding fragment thereof may induce the activation of the Tie2 receptor. Such activation of Tie2 receptor may be induced by an increase in the phosphorylation of Tie2 receptor and/or the phosphorylation of proteins related to the downstream signal pathway thereof, for example, at least one selected from the group consisting of Akt (NM_005163), eNOS (NM_000603), 42/44 (NM_002745), etc. Also, the anti-Ang2 antibody or an antigen-binding fragment thereof may induce the intracellular internalization of a Tie2 receptor. In other words, the anti-Ang2 antibody or an antigen-binding fragment thereof may bind to Ang2 and the Tie2 receptor via Ang2 to form a complex and induce the activation of the Tie2 receptor, by not inhibiting binding between Ang2 and the Tie2 receptor while specifically binding to Ang2, unlike the pre-existing anti-Ang2 antibodies. Therefore, the anti-Ang2 antibody or an antigen-binding fragment thereof may increase the phosphorylation of a protein related to the downstream signal pathway of Tie2 receptor, such as at least one selected from the group consisting of Akt, eNOS, and 42/44, compared to the case using (treating) no antibody or any anti-Ang2 antibody inhibiting the binding between Ang2 and Tie2 receptor, such as antibody 4H10 (SEQ ID NOs: 12 & 13), RG antibody (Regeneron Co.), etc.

The Ang2 protein which functions as an antigen against the antibody is closely related to angiogenesis, and as a soluble ligand present in blood, it is widely involved in angiogenesis, metastasis, cancer cell invasion, etc. The Ang2 may be derived from mammals including primates such as humans and monkeys and rodents such as rats and mice and for example, it may be human Ang2 (e.g., NCBI Accession No. O15123, etc.), monkey Ang2 (e.g., NCBI Accession No. Q8MIK6, etc.), mouse Ang2 (e.g., NCBI Accession No. O35608, etc.), and rat Ang2 (e.g., NCBI Accession No. O35462, etc.), but is not limited thereto.

The Tie2 receptor (TEK tyrosine kinase), which is an Angiopoietin-1 receptor, is expressed in vascular endothelial cells in various mammals such as mouse (NM_013690; NP_038718), rat, and human (NM_000459; NP_000450), and is involved in various downstream signaling.

As explained above, the anti-Ang2 antibody or an antigen-binding fragment thereof is characterized in that the antibody which specifically binds to Ang2 but does not inhibit binding between Ang2 and Tie2 receptor and forms a complex (antibody/Ang2/Tie2) together with Ang2 and the Tie2 receptor, has a characteristic of inducing the dimerization of the antibody, and through this, it can induce the activation of the Tie2 receptor and its downstream signaling by effectively clustering the Tie2 receptor which constitutes the complex. By virtue of such an action mechanism, the antibody and the antigen-binding fragment thereof inhibits Ang2 functions by binding to Ang2 to induce the intracellular internalization and degradation thereof and thus lowers the level of circulating Ang2 and at the same time, it induces Tie2 downstream signaling by binding to the Tie2 receptor together with Ang2 to activate the Tie2 receptor, like Ang1 and induces the stabilization of vascular endothelial cells. By having such dual functions, the antibody and the antigen-binding fragment thereof can be usefully employed to treat not only symptoms (disorders) due to the overexpression of Ang2 but also symptoms (disorders) due to the decrease in the stabilization of vascular endothelial cells, that is, the increase of vascular penetration.

The anti-Ang2 antibody or an antigen-binding fragment thereof may recognize all or part (for example, at least one amino acid selected from the group consisting of the amino acid residue site exposed to the outside of loop) of loop 1 (of SEQ ID NO: 11, a site from $417^{th}$ amino acid to $434^{th}$ amino acid) of human Ang2 (hAng2; SEQ ID NO: 11; Accession #O15123) or an amino acid sequence site including 2 to 20, 2 to 15, 2 to 10, or 2 to 5 contiguous amino acids including at least one amino acid residue exposed to the outside of loop 1 of SEQ ID NO: 11 as an epitope, or specifically bind to this site.

```
Ang2
                                                    (SEQ ID NO: 11)
MWQIVFFTLS CDLVLAAAYN NFRKSMDSIG KKQYQVQHGS

CSYTFLLPEM DNCRSSSSPY VSNAVQRDAP LEYDDSVQRL

QVLENIMENN TQWLMKLENY IQDNMKKEMV EIQQNAVQNQ

TAVMIEIGTN LLNQTAEQTR KLTDVEAQVL NQTTRLELQL

LEHSLSTNKL EKQILDQTSE INKLQDKNSF LEKKVLAMED

KHIIQLQSIK EEKDQLQVLV SKQNSIIEEL EKKIVTATVN

NSVLQKQQHD LMETVNNLLT MMSTSNSAKD PTVAKEEQIS

FRDCAEVFKS GHTTNGIYTL TFPNSTEEIK AYCDMEAGGG

GWTIIQRRED GSVDFQRTWK EYKVGFGNPS GEYWLGNEFV

SQLTNQQRYV LKIHLKDWEG NEAYSLYEHF YLSSEELNYR

IHLKGLTGTA GKISSISQPG NDFSTKDGDN DKCICKCSQM

LTGGWWFDAC GPSNLNGMYY PQRQNTNKFN GIKWYYWKGS

GYSLKATTMM IRPADF
```

For example, the anti-Ang2 antibody may recognize Q418, P419, a combination of Q418 and P419 positioned at loop 1 of SEQ ID NO: 11, or an amino acid sequence site including 2 to 20, 2 to 15, 2 to 10, or 2 to 5 contiguous amino acids including the amino acid residue of Q418, P419, or combination of Q418 and P419 of SEQ ID NO: 11 as an epitope, or specifically bind to this site. In one embodiment, the anti-Ang2 antibody may recognize the amino acid residues of Q418 and P419 of SEQ ID NO: 11 as an epitope, or specifically bind to this portion.

Q418, P419, or an amino acid site including them, to which the anti-Ang2 antibody specifically binds, is an exposed amino acid residue positioned at loop 1 of the three dimensional structure of Ang2, and it is considered to directly participate in binding between Ang2 and Tie2 receptor or to be a site regulating it.

In Q418, P419, or an amino acid site including them, to which the anti-Ang2 antibody specifically binds, the term "contiguous amino acid" may refer to amino acids which are adjacent to one another on primary, secondary, or tertiary structure of a protein.

As not only the anti-Ang2 antibody recognizing and/or specifically binding to the above site but also an antibody or an antigen-binding fragment thereof which competes with the anti-Ang2 antibody for binding can inhibit Ang2 and at the same time, form a complex with Ang2 and Tie2 receptor (i.e., by binding of antibody-Ang2 to the Tie2 receptor) to activate Tie2. This competitively-binding antibody may be an antibody recognizing a site adjacent to the aforementioned site on its three dimensional structure as an epitope and/or a specific binding site. The competitively-binding antibody may have a binding affinity with Ang2 of 0.1 pM to 50 nM, particularly 1 pM to 30 nM, 2 pM to 20 nM, or 1 nM to 10 nM.

Therefore, the anti-Ang2 antibody or an antigen-binding fragment thereof may be at least one selected from the group consisting of an antibody or an antigen-binding fragment thereof recognizing the aforementioned site as an epitope or specifically binding thereto.

In a particular embodiment, the anti-Ang2 antibody or an antigen-binding fragment thereof may comprise or consist essentially of:

at least one heavy chain complementarity determining region (CDR) selected from the group consisting of a polypeptide (CDR-H1) including the amino acid sequence of SEQ ID NO: 1, a polypeptide (CDR-H2) including the amino acid sequence of SEQ ID NO: 2, and a polypeptide (CDR-H3) including the amino acid sequence of SEQ ID NO: 3, or a heavy chain variable region including the at least one heavy chain complementarity determining region;

at least one light chain complementarity determining region selected from the group consisting of a polypeptide (CDR-L1) including the amino acid sequence of SEQ ID NO: 4, a polypeptide (CDR-L2) including the amino acid sequence of SEQ ID NO: 5, and a polypeptide (CDR-L3) including the amino acid sequence of SEQ ID NO: 6, or a light chain variable region including the at least one light chain complementarity determining region;

a combination of said at least one heavy chain complementarity determining region and said at least one light chain complementarity determining region; or a combination of the heavy chain variable region and the light chain variable region.

More particularly, the anti-Ang2 antibody or an antigen-binding fragment thereof may comprise or consist essentially of:

a heavy chain complementarity determining region including a polypeptide (CDR-H1) including the amino acid sequence of SEQ ID NO: 1, a polypeptide (CDR-H2) including the amino acid sequence of SEQ ID NO: 2, and a polypeptide (CDR-H3) including the amino acid sequence of SEQ ID NO: 3, or a heavy chain variable region including the at least one heavy chain complementarity determining region; and a light chain complementarity determining region including a polypeptide (CDR-L1) including the amino acid sequence of SEQ ID NO: 4, a polypeptide (CDR-L2) including the amino acid sequence of SEQ ID NO: 5, and a polypeptide (CDR-L3) including the amino acid sequence of SEQ ID NO: 6, or a light chain variable region including the at least one light chain complementarity determining region.

In particular, the heavy chain complementarity determining region of the anti-Ang2 antibody or an antigen-binding fragment thereof may have amino acid sequences, for example, as set forth in the following Table 1.

TABLE 1

| Heavy Chain CDR Amino Acid Sequences | | |
|---|---|---|
| CDRH1-KABAT | CDRH2-KABAT | CDRH3-KABAT |
| SDYAWN (SEQ ID NO: 1) | YINYSGNTDYNPSLKS (SEQ ID NO: 2) | GNFEGAMDY (SEQ ID NO: 3) |

Likewise, the light chain complementarity determining region of the anti-Ang2 antibody or an antigen-binding fragment thereof may have amino acid sequences, for example, as set forth in the following Table 2.

TABLE 2

| Light Chain CDR Amino Acid Sequences | | |
|---|---|---|
| CDRL1-KABAT | CDRL2-KABAT | CDRL3-KABAT |
| KASQSVSNDVA (SEQ ID NO: 4) | YASNRYP (SEQ ID NO: 5) | QQDYSSPWT (SEQ ID NO: 6) |

In one embodiment, the heavy chain variable region of the antibody or the antigen-binding fragment thereof may include the amino acid sequence of SEQ ID NO: 7:

(SEQ ID NO: 7)
DVQLQESGPGLVKPSQSLSLTCTVTGYSITSDYAWNWIRQFPGNKLEWMG

YINYSGNTDYNPSLKSRSSITRDTSKNQFFLQLNSVTTGDTATYYCARGN

FEGAMDYWGQGTSVTVSS (In SEQ ID NO: 7 above, the underlined bold letters are CDRH1, CDRH2, and CDRH3 in sequence)

The light chain of the antibody according to one embodiment may include the amino acid sequence of SEQ ID NO: 9.

(SEQ ID NO: 9)
SIVMTQTPKFLLVSAGDRVTITCKASQSVSNDVAWYQQKPGQSPKLLIYY

ASNRYPGVPDRFTGSGYGTDFTFTISTVQAEDLAVYFCQQDYSSPWTFGG

GTKLEIK (In SEQ ID NO: 9 above, the underlined bold letters are CDRL1, CDRL2, and CDRL3 in sequence)

In this regard, the anti-Ang2 antibody or an antigen-binding fragment thereof may include a heavy chain variable region including the amino acid sequence of SEQ ID NO: 7, a light chain variable region including the amino acid sequence of SEQ ID NO: 9, or a combination of the heavy chain variable region and the light chain variable region.

For example, the anti-Ang2 antibody or an antigen-binding fragment thereof may include a heavy chain variable region including the amino acid sequence of SEQ ID NO: 7 and a light chain variable region including the amino acid sequence of SEQ ID NO: 9.

In one embodiment, the anti-Ang-2 antibody or the antigen-binding fragment thereof may not consist merely of at least one amino acid sequence selected from the group consisting of SEQ ID NO: 1, SEQ ID NO: 3, SEQ ID NO: 4, and SEQ ID NO: 5.

In another embodiment, a method is provided for screening a candidate agent (anti-Ang2 antibody) for diagnosing, preventing, and/or treating a disease related to Ang2 overexpression, angiogenesis, increase of vascular permeability, and/or a decrease of normal blood vessel formation using the above epitope, for example, a method for screening an anti-Ang2 antibody. The screening method may comprise or consist essentially of:

(a) contacting a candidate compound to the three dimensional structure epitope of the aforementioned Angiopoietin-2; and (b) measuring binding between the epitope and the candidate compound, for example, in the presence of a Tie2 receptor.

The screening method may further include step (c) of identifying binding between Ang2 and Tie2 receptor. The step (c) is to identify whether the candidate compound inhibits binding between Ang2 and Tie2 receptor and it may be performed before or after the step (b), or simultaneously with it. Through the step (c), an anti-Ang2 antibody which binds to Ang2 but does not inhibit binding between Ang2 and Tie2 receptor, i.e., having a characteristic of inducing binding between Ang2 and Tie2 receptor can be screened.

In the antibody screening method, when the binding between the epitope and the candidate compound is detected, the candidate compound may be determined as a candidate agent (anti-Ang2 antibody). Therefore, the antibody screening method may further comprise, after step (b) or (c), a step of determining the candidate compound as a candidate agent (anti-Ang2 antibody) when the binding between the epitope and the candidate compound is detected.

Furthermore, the screening method may further include step (d) of identifying the inhibition of Ang2 and/or the activation of Tie2 receptor, and they can be included in any order. Through the step (d), an anti-Ang2 antibody which binds to Ang2 to inhibit the activity thereof but binds to Ang2 to induce binding between Ang2 and Tie2 receptor and exhibits Tie2 receptor activation effects, like Ang1, can be screened.

In the above screening method, when the epitope and the candidate compound show binding affinity (kd) in the range of 10 nM or less, for example, 0.1 pM to 10 nM, or 10 pM to 10 nM, or 100 pM to 10 nM, or when binding between Ang2 and Tie2 receptor is identified (i.e., in case that the candidate compound does not inhibit binding between Ang2 and Tie2 receptor) while the epitope and the candidate compound still show such binding affinity, the candidate compound can be determined to be a candidate for diagnosing, preventing, and/or treating a disease related to Ang2 overexpression, angiogenesis, increase of vascular permeability, and/or decrease of normal blood vessel formation, for example, an anti-Ang2 antibody candidate.

The epitope may be all or part (for example, at least one selected from the group consisting of the amino acid residue site exposed to the outside of loop 1) of loop 1 (of SEQ ID NO: 11, a site from $417^{th}$ amino acid to $434^{th}$ amino acid) of human Ang-2 (hAng-2; SEQ ID NO: 11; Accession #O15123) or an amino acid sequence site including 2 to 20, 2 to 15, or 2 to 10 contiguous amino acids including at least one amino acid residue exposed to the outside of loop 1 of SEQ ID NO: 11 and for example, it may be at least one selected from the group consisting of Q418, P419, a combination of Q418 and P419 positioned at loop 1 of SEQ ID NO: 11, or an amino acid sequence site including 2 to 20, 2 to 15, 2 to 10, or 2 to 5 contiguous amino acids including the same.

The candidate compounds may be one or more selected from the group consisting of various artificially-synthesized or natural compounds, polypeptides, oligopeptides, peptide or protein scaffolds (for example, antibody, peptibody, nanobody, etc.), polynucleotides, oligonucleotides, antisense-RNA, shRNA (short hairpin RNA), siRNA (small interference RNA), aptamers, natural product extracts and so on.

The step of measuring the binding affinity between the epitope and the candidate compound may be carried out using various methods known in the art. For example, the binding affinity may be measured using a Biacore machine. In general, the range within which the binding affinity is considered as a therapeutic drug may be defined to have a binding constant KD value of not greater than 10 mM. For instance, in case that the binding affinity between the epitope of Angiopoietin-2 and a specimen to be analyzed (for example, antibody) is 0.1 pM to 50 nM, particularly 0.5 pM to 35 nM, more particularly 1 pM to 10 nM when measured using surface plasmon resonance methods such as a Biacore machine, the specimen (for example, antibody) can be determined to be a candidate for diagnosing, preventing, and/or treating a disease related to Ang2 overexpression, angiogenesis, increase of vascular permeability, and/or decrease of normal blood vessel formation.

The identification of the presence of binding between Ang2 and Tie2 and the identification of Ang2 inhibition and the activation of Tie2 receptor will be described later.

In another embodiment, a polypeptide molecule is provided including the heavy chain complementarity determining region, the light chain complementarity determining region or the combination thereof; or the heavy chain variable region, the light chain variable region or the combination thereof of the anti-Ang2 antibody as described above. The polypeptide molecule may function as a precursor or a component of an antagonist against Ang2 as well as for manufacturing an antibody or an antigen-binding fragment thereof. For example, the polypeptide molecule may function as an Ang2 antigen binding site, and can be included as a component of a protein scaffold (e.g., peptibody, nanobody, etc.), a bispecific antibody, and a multi-specific antibody having a similar structure to an antibody.

The term "antagonist" as used herein is interpreted to encompass all molecules that partially or entirely block, suppress or neutralize at least one biological activity of its target (e.g., Ang2).

The term "peptibody (peptide+antibody)" used herein refers to a fusion protein including a peptide and all or part of the constant region of an antibody such as an Fc portion wherein the peptide serves as an antigen binding site (heavy chain and/or light chain CDR or variable regions) thereby to render a protein having similar framework and functions to an antibody The term "nanobody" used herein is called a single-domain antibody, refers to an antibody fragment including a single variable domain of an antibody as a monomer form, and has characteristics of selectively binding to a specific antigen similarly to an antibody having an intact structure. The molecular weight of the nanobody is generally about 12 kDa to about 15 kDa, which is very little when compared to the normal molecular weight (about 150 kDa or about 160 kDa) of an intact antibody (including two heavy chains and two light chains) and in some cases it is smaller than an Fab fragment or scFv fragment.

The term "bispecific antibody" or "multi-specific antibody" used herein refers to an antibody recognizing and/or binding to two (bispecific antibody) or more (multi-specific antibody) different antigens, or recognizing and/or binding to different sites of the same antigen, and one antigen binding site of the bispecific antibody or multi-specific antibody may include the polypeptide described above.

In a specific embodiment, the polypeptide molecule may comprise or consist essentially of:

at least one selected from the group consisting of a polypeptide including the amino acid sequence of SEQ ID NO: 1, a polypeptide including the amino acid sequence of SEQ ID NO: 2, and a polypeptide including the amino acid sequence of SEQ ID NO: 3;

at least one selected from the group consisting of a polypeptide including the amino acid sequence of SEQ ID NO: 4, a polypeptide including the amino acid sequence of SEQ ID NO: 5, and a polypeptide including the amino acid sequence of SEQ ID NO: 6; or a combination thereof.

In a specific embodiment, the polypeptide molecule may comprise or consist essentially of the amino acid sequence of SEQ ID NO: 8, the amino acid sequence of SEQ ID NO: 9, or a combination thereof.

In one embodiment, the polypeptide molecule may not consist merely of at least one amino acid sequence selected from the group consisting of SEQ ID NO: 1, SEQ ID NO: 3, SEQ ID NO: 4, and SEQ ID NO: 5.

As described above, the above bispecific antibody or multi-specific antibody is referred to as an antibody including each antigen binding site to different two or more kinds of antigens and recognizing and/or binding to the two or more kinds of antigens at the same time, wherein one of the antigen binding sites may include the aforementioned polypeptide molecule. In particular, the polypeptide molecule serving as Ang2 antigen binding site may form a dimer or multimer together with an antigen binding site to another antigen to constitute a bi-specific antibody or a multi-specific antibody. Accordingly, in one embodiment, there is provided a bi-specific antibody or a multi-specific antibody including the polypeptide molecule as an Ang2 antigen binding site.

In another embodiment, there is provided a protein scaffold including at least one (e.g., 1 to 5, or 2 to 4) peptide complex including one or more of the aforementioned polypeptide molecules or a repeat where the polypeptide molecules are repeatedly linked by a linker (hereafter, 'first peptide'), and a polypeptide having a structural function (hereafter, 'second peptide'; e.g., a heavy chain or light chain constant region of an antibody (IgG (IgG1, IgG2, IgG3, or IgG4), IgA, IgE, IgD, IgM, etc.), or an Fc fragment of an antibody) wherein said at least one peptide complex is bound to at the second peptide (e.g., Fc fragment) to form a multimer structure.

Another embodiment provides a polynucleotide encoding the polypeptide molecule, a recombinant vector comprising the polynucleotide, and a recombinant cell comprising (transfected with) the recombinant vector.

The term "vector" used herein refers to a means for expressing a target gene in a host cell. For example, it includes a plasmid vector, a cosmid vector, and a virus vector such as a bacteriophage vector, an adenovirus vector, a retrovirus vector and an adeno-associated virus vector. Suitable recombinant vectors may be constructed by manipulating plasmids often used in the art (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), a phage (for example, λgt4λB, λ-Charon, λΔz1, and M13), or a virus (for example, SV40).

The recombinant vector may include the polynucleotides encoding the protein complex and an expression regulating factor (sequence) such as promoter, which are operatively linked to each other. The term "operatively linked" used herein refers to a functional linkage between a nucleotide expression regulating sequence (for example, a promoter sequence) and other nucleotide sequences. Thus, the expression regulating sequence may regulate the transcription and/or translation of the other nucleotide sequences by being operatively linked.

The recombinant vector may be constructed typically for either cloning or expression. The expression vector may be any ordinary vectors known in the pertinent art for expressing an exogenous protein in plants, animals, or microorganisms. The recombinant vector may be constructed using various methods known in the art.

The recombinant vector may be constructed using a prokaryotic cell or a eukaryotic cell as a host. For example, when a prokaryotic cell is used as a host cell, the expression vector used generally includes a strong promoter capable of initiating transcription (for example, pL$^\lambda$ promoter, CMV promoter, trp promoter, lac promoter, tac promoter, T7 promoter, etc.), a ribosome binding site for initiating translation, and a transcription/translation termination sequence. When a eukaryotic cell is used as a host cell, the vector used generally includes the origin of replication acting in the eukaryotic cell, for example, a f1 replication origin, a SV40 replication origin, a pMB1 replication origin, an adeno replication origin, an AAV replication origin, or a BBV replication origin, but is not limited thereto. A promoter in an expression vector for a eukaryotic host cell may be a promoter derived from the genomes of mammalian cells (for example, a metallothionein promoter) or a promoter derived from mammalian viruses (for example, an adenovirus late promoter, a vaccinia virus 7.5K promoter, a SV40 promoter, a cytomegalovirus promoter, and a tk promoter of HSV). A transcription termination sequence in an expression vector for a eukaryotic host cell may be, in general, a polyadenylation sequence.

The recombinant cell may be those obtained by transfecting the recombinant vector into a suitable host cell. Any host cells known in the pertinent art to enable stable and continuous cloning or expression of the recombinant vector may be used as the hose cell. Suitable prokaryotic host cells may include *E. coli* JM109, *E. coli* BL21, *E. coli* RR1, *E. coli* LE392, *E. coli* B, *E. coli* X 1776, *E. coli* W3110, *Bacillus* species strains such as *Bacillus subtillis* or *Bacillus thuringiensis*, intestinal bacteria and strains such as *Salmonella typhymurum, Serratia marcescens*, and various *Pseudomonas* species. Suitable eukaryotic host cells to be transformed may include yeasts, such as *Saccharomyces cerevisiae*, insect cells, plant cells, and animal cells, for example, Sp2/0, Chinese hamster ovary (CHO) K1, CHO, CHO-s, HEK293, HEK293f, DG44, PER.C6, W138, BHK, COS-7, 293, HepG2, Huh7, 3T3, RIN, and MDCK cell lines, but are not limited thereto.

The polynucleotide or the recombinant vector including the same may be transferred (transfected) into a host cell by using known transfer methods. Suitable transfer methods for prokaryotic host cells may include a method using $CaCl_2$ and electroporation. Suitable transfer methods for eukaryotic host cells may include microinjection, calcium phosphate precipitation, electroporation, liposome-mediated transfection, and gene bombardment, but are not limited thereto.

A transformed host cell may be selected using a phenotype expressed by a selected marker by any methods known in the art. For example, if the selected marker is a gene that is resistant to a specific antibiotic, a transformant may be easily selected by being cultured in a medium including the antibiotic.

The antibody includes any animal-derived antibodies, chimeric antibodies, humanized antibodies and human antibodies. An animal-derived antibody which is produced by immunizing an animal with a desired antigen may generally trigger an immune rejection response when administered to humans for treatment purpose, and a chimeric antibody has been developed to suppress such immune rejection response. A chimeric antibody is formed by replacing the constant region of an animal-derived antibody, which is a cause of anti-isotype response, with the constant region of a human antibody using genetic engineering methods. The chimeric antibody has considerably improved anti-isotype response in comparison with animal-derived antibodies, but animal-derived amino acids are still present in its variable regions and thus it still contains potential side effects resulting from an anti-idiotypic response. It is a humanized antibody that has been thus developed to improve such side effects. This is manufactured by grafting CDR (complementarity determining regions) which, of the variable regions of a chimeric antibody, has an important role in antigen binding into a human antibody framework.

An important consideration in CDR grafting technology for manufacturing a humanized antibody is to select an optimized human antibody which can receive best the CDR of an animal-derived antibody and for this, utilization of antibody database, analysis of crystal structure, molecule modeling technology, etc. are employed. However, although the CDR of an animal-derived antibody is grafted into an optimized human antibody framework, there are a considerable number of cases where antigen binding affinity is not preserved because there are amino acids which affect antigen binding while being positioned at the framework of the animal-derived antibody. In this regard, it may be essential to apply an additional antibody engineering technology for restoring antigen binding affinity.

According to one embodiment, the antibody may be a mouse-derived antibody, a mouse-human chimeric antibody, a humanized antibody, or a human antibody. The antibody or an antigen-binding fragment thereof may be isolated from a living body or non-naturally occurring. The antibody or an antigen-binding fragment thereof may be recombinant or synthetic.

Antibodies have been widely used for treating diseases. As antibodies are very stable in vivo as well as in vitro and have a long half-life, they are favorable for mass expression and production. Also, since an antibody has intrinsically a dimer structure, it has a fairly high avidity.

An intact antibody has a structure with two full-length light chains and two full-length heavy chains, and each light chain is linked to each heavy chain via a disulfide bond. The constant region of an antibody is divided into a heavy chain constant region and a light chain constant region, and the heavy chain constant region has gamma ($\gamma$), mu ($\mu$), alpha ($\alpha$), delta ($\delta$) and epsilon ($\epsilon$) types, and has gamma1 ($\gamma$1), gamma2 ($\gamma$2), gamma3 ($\gamma$3), gamma4 ($\gamma$4), alpha1 ($\alpha$1) and alpha2 ($\alpha$2) as its subclass. The light chain constant region has kappa ($\kappa$) and lambda ($\lambda$) types.

The term "heavy chain" is understood to include a full-length heavy chain and fragments thereof, the full-length heavy chain including a variable region domain $V_H$ including an amino acid sequence having sufficient variable region sequences that contribute the specificity for antigen binding and three constant region domains $C_{H1}$, $C_{H2}$ and $C_{H3}$ domains and a hinge. The term "light chain" is understood to include a full-length light chain and fragments thereof, the full-length light chain including a variable region domain $V_L$ including an amino acid sequence having sufficient variable region sequences that contribute to the specificity for antigen binding and a constant region domain $C_L$.

The term "CDR (complementarity determining region)" refers to an amino acid sequence found in the hypervariable region of a heavy chain and a light chain of an immunoglobulin. The heavy and light chain may each include three CDRs (CDRH1, CDRH2, CDRH3, and CDRL1, CDRL2, CDRL3). The CDRs of an antibody can provide an essential contact residue for binding to an antigen or an epitope. Throughout the specification, the terms "specifically binding" or "specifically recognizing" has the same meaning as generally known to an ordinary person in the art, indicating that an antigen and an antibody specifically interact with each other to lead to an immunological response.

The antigen binding site of an antibody may be a fragment including at least one complementarity determining region.

The term "antigen-binding fragment," which is a fragment of the full structure of an immunoglobulin, refers to some of a polypeptide including a portion to which an antigen can bind. For example, it may be an scFv, an (scFv)$_2$, an scFv-Fc, an Fab, an Fab' or an F(ab')$_2$, but is not limited thereto.

Among the above antigen-binding fragments, an Fab, which is a structure having the light chain and heavy chain variable regions, the light chain constant region, and the heavy chain first constant region ($C_{H1}$), has one antigen binding site. An Fab' differs from the Fab in that the Fab' has a hinge region including at least one cysteine residue at the C-terminal of the heavy chain $C_{H1}$ domain. An F(ab')$_2$ is produced when cysteine residues at the hinge region of Fab' are joined by a disulfide bond. An Fv is a minimal antibody fragment, having only heavy chain variable regions and light chain variable regions, and a recombinant technique for producing the Fv fragment is well known in the art. In a two-chain Fv fragment, the heavy chain variable domains are associated with the light chain variable domains via a non-covalent bond. A single-chain Fv fragment has a structure in which a heavy chain variable domain and a light chain variable domain are covalently joined to each other via a covalent bond or directly at the C-terminus, so that it can form a dimer as in a two-chain Fv fragment. In this context, the heavy chain variable region and the light chain variable region may be connected with each other through a linker, e.g., a peptide linker, or directly. The peptide linker may be composed of 1 to 100 amino acid residues, or 2 to 50 amino acid residues, with no limitations imposed on the kind of the amino acid residues. For example, the peptide linker may include Gly, Asn and/or Ser, and may also include neutral amino acids such as Thr and/or Ala. Amino acid sequences suitable for use in the peptide linker may be those well known in the art. So long as it has no negative influence on the function of the antigen-binding fragment, the length of the peptide linker may be appropriately adjusted. For example, the peptide linker may be an amino acid sequence composed of 1 to 100, 2 to 50, or 5 to 25 amino acid residues selected from among Gly, Asn, Ser, Thr, Ala, and a combination thereof. By way of example, the peptide linker may be (G4S)n (wherein n represents the repeating number of (G4S) and may be an integer of 1 to 10, e.g., 2 to 5).

The antigen-binding fragment may be obtained using a protease (for example, a whole antibody can be digested with papain to obtain Fab fragments, or can be digested with pepsin to obtain F(ab')$_2$ fragments), or may be prepared by a genetic recombinant technique.

The term "hinge region" refers to a region included in the heavy chains of an antibody, which is present between the CH1 and CH2 regions, and provides flexibility to the antigen binding site in the antibody. For example, the hinge may be derived from a human antibody and particularly, it may be derived from IgA, IgE, IgD, IgM, or IgG, for example, IgG1, IgG2, IgG 3, or IgG4.

When an animal-derived antibody goes through a chimerization process, an animal-derived IgG1 hinge is replaced with a human IgG1 hinge, but a length of the animal-derived IgG1 hinge is shorter than the human IgG1 hinge, and disulfide bonds between two heavy chains are reduced from 3 to 2. Thus, rigidity of the hinges may have different effects.

Therefore, modification of a hinge region can increase an antigen binding efficiency of a humanized antibody. Methods of deleting, inserting, or substituting an amino acid for modifying amino acid sequences of the hinge region are well known in the art.

Portions (e.g., constant regions) except the CDRs or variable regions of the anti-Ang2 antibody may be derived from a human antibody and particularly, they may be derived from IgA, IgD, IgE, IgD, IgM, or IgG, for example, IgG1, IgG2, IgG 3, or IgG4.

The anti-Ang2 antibody may be a monoclonal antibody. The monoclonal antibody may be prepared by methods well known in the art. For example, it may be prepared using a phage display technique. Alternately, the Ang2 antibody may be prepared into a mouse-derived monoclonal antibody by methods set forth in the paper written by Schwaber, et al (Schwaber, J and Cohen, E. P., "Human×Mouse Somatic Cell Hybrid Clones Secreting Immunoglobulins of Both Parental Types," Nature, 244 (1973), 444-447).

Meanwhile, individual monoclonal antibodies may be screened using a typical ELISA (Enzyme-Linked ImmunoSorbent Assay) format, based on the binding potential with Ang2. Inhibitory activities can be verified through functional analysis such as competitive ELISA for verifying the molecular interaction of binding assemblies or functional analysis such as a cell-based assay. Then, with regard to monoclonal antibody members selected on the basis of their strong inhibitory activities, their affinities (Kd values) to Ang2 may be each verified.

The rest portions not including the antigen binding portions of the finally selected antibodies may be prepared as not only human immunoglobulin antibodies but also humanized antibodies. Preparation of humanized antibodies is well known in the art (Almagro, J. C. and Fransson, J., "Humanization of antibodies," Frontiers in Bioscience, 13(2008), 1619-1633).

Another embodiment provides a hybridoma cell line which produces a monoclonal antibody of the anti-Ang2 antibody. The hybridoma cell line may be a cell line having accession number (KCLRF-BP-00295).

As described above, the anti-Ang2 antibody or an antigen-binding fragment thereof is characterized by binding to Ang2 while not inhibiting Ang2 from binding to Tie2 receptor and inducing binding between Ang2 and Tie2. Also, a conjugate formed from binding of the anti-Ang2 antibody or an antigen-binding fragment thereof and Ang2 is characterized by binding to a Tie2 receptor (wherein an Ang2 portion of the conjugate participates in binding), just like Ang1, to activate the Tie2 receptor.

Hence, another embodiment provides a conjugate of Ang2 and an anti-Ang2 antibody in which the anti-Ang2 antibody or an antigen-binding fragment thereof and Ang2 are bound to each other. Another embodiment provides a composition for inducing binding of Ang2 with a Tie2 receptor, including the conjugate of Ang2 and an anti-Ang2 antibody as an active ingredient. Another embodiment provides a method for inducing binding of Ang2 with a Tie2 receptor, including administering the conjugate of Ang2 and an anti-Ang2 antibody to a subject. The subject may be in need of binding between Ang2 and Tie2 receptor. The method for inducing binding of Ang2 with Tie2 receptor may further include a step of identifying a subject who is in need of binding between Ang2 and Tie2 receptor, prior to the administration step. Still another embodiment provides a composition for activating a Tie2 receptor including the conjugate of Ang2 and an anti-Ang2 antibody as an active ingredient. Still another embodiment provides a method for activating a Tie2 receptor including administering the conjugate of Ang2 and an anti-Ang2 antibody to a subject. The subject may be in need of activating the Tie2 receptor. The Tie2 receptor activation method may further include a step of identifying a subject who is in need of activating the Tie2 receptor, prior to the administration step. The subject may be mammals including primates such as humans and monkeys or rodents such as rats and mice, or cells, tissues, or body fluids (e.g., blood, serum, etc.) isolated therefrom or artificially cultured. Another embodiment provides a use of the conjugate of Ang2 and an anti-Ang2 antibody for activating a Tie2 receptor.

As described above, since the anti-Ang2 antibody or an antigen-binding fragment thereof has a function of inhibiting abnormal angiogenesis by inhibiting the functions of Ang2, it is applicable to prevent, alleviate, improve, and/or treat various diseases (e.g., cancer) related to abnormal angiogenesis (see Example 13). Moreover, since the anti-Ang2 antibody or an antigen-binding fragment thereof does not inhibit binding between Ang2 and Tie2 (see Example 3 and FIG. 1), it can activate a Tie2 signaling (see Example 6 and FIG. 3) by activating Tie2 (see Example 6 and FIG. 3), and it accelerates the formation of vascular endothelium or lymphatic endothelium and increases mobility (see Example 10) to suppress vascular permeability increase (see Example 11), whereby it is applicable to prevent, alleviate, improve, and/or treat various diseases related to vascular permeability (for example, sepsis, eye disorders, etc.). Also, as described above, since the anti-Ang2 antibody or an antigen-binding fragment thereof accelerates the formation of vascular endothelium or lymphatic endothelium to increase the formation of healthy blood vessels and normalize the blood vessels, it is also applicable to prevent, alleviate, improve, and/or treat various diseases or symptoms requiring the formation of healthy blood vessels such as wound healing or ischemic disorders, and it reduces cancer growth and metastasis possibility by changing the abnormally formed cancer blood vessels into structurally and functionally normal forms. Moreover, the anti-Ang2 antibody or an antigen-binding fragment thereof has an effect of suppressing inflammatory response (see Example 12), whereby it is applicable to prevent, alleviate, improve, and/or treat various inflammatory disorders.

Another embodiment provides a pharmaceutical composition for inhibiting angiogenesis including the anti-Ang2 antibody or an antigen-binding fragment thereof as an active ingredient. Another embodiment provides a method for inhibiting angiogenesis including administering a pharmaceutically effective amount of the anti-Ang2 antibody or an antigen-binding fragment thereof to a subject. The subject may be in need of inhibiting angiogenesis. The angiogenesis inhibition method may further include a step of identifying a subject who is in need of the inhibition of angiogenesis, prior to the administration step.

Another embodiment provides a pharmaceutical composition for reducing vascular permeability including the anti-Ang2 antibody or an antigen-binding fragment thereof as an active ingredient. Another embodiment provides a method for reducing vascular permeability including administering a pharmaceutically effective amount of the anti-Ang2 antibody or an antigen-binding fragment thereof to a subject. The subject may be in need of the reduction of vascular permeability. The vascular permeability reduction method may further include a step of identifying a subject who is in need of the reduction of vascular permeability, prior to the administration step.

Another embodiment provides a pharmaceutical composition for preventing and/or treating a disease related to Ang2 overexpression, angiogenesis, and/or vascular permeability increase including the anti-Ang2 antibody or an antigen-binding fragment thereof as an active ingredient. Another embodiment provides a method for preventing and/or treating a disease related to Ang2 overexpression, angiogenesis, and/or vascular permeability increase including administering a pharmaceutically effective amount of the anti-Ang2 antibody or an antigen-binding fragment thereof to a subject. The subject may be in need of preventing and/or treating the disease related to Ang2 overexpression, angiogenesis, and/or vascular permeability increase. The prevention and/or treatment method may further include a step of identifying a subject who is in need of preventing and/or treating a disease related to Ang2 overexpression, angiogenesis, and/or vascular permeability increase, prior to the administration step.

Another embodiment provides a pharmaceutical composition for inducing normal blood vessel formation including the anti-Ang2 antibody or an antigen-binding fragment thereof as an active ingredient. Another embodiment provides a method of inducing normal blood vessel formation, including administering a pharmaceutically effective amount of the anti-Ang2 antibody or an antigen-binding fragment thereof to a subject. The subject may be in need of inducing normal blood vessel formation. The method of inducing normal blood vessel formation may further include a step of identifying a subject who is in need of inducing normal blood vessel formation, prior to the administration step.

Another embodiment provides a pharmaceutical composition for preventing and/or treating a disease related to normal blood vessel formation decrease including the anti-Ang2 antibody or an antigen-binding fragment thereof as an active ingredient. Another embodiment provides a method for preventing and/or treating a disease related to normal blood vessel formation decrease including administering a pharmaceutically effective amount of the anti-Ang2 antibody or an antigen-binding fragment thereof to a subject. The subject may be in need of preventing and/or treating the disease related to normal blood vessel formation decrease. The prevention and/or treatment method may further include a step of identifying a subject who is in need of preventing and/or treating a disease related to normal blood vessel formation decrease, prior to the administration step.

Another embodiment provides a pharmaceutical composition for tissue regeneration and/or wound healing including the anti-Ang2 antibody or an antigen-binding fragment thereof as an active ingredient. Another embodiment provides a method for tissue regeneration and/or wound healing including administering a pharmaceutically effective amount of the anti-Ang2 antibody or an antigen-binding fragment thereof to a subject. The subject may be in need of tissue regeneration and/or wound healing. The method may further include a step of identifying a subject who is in need of tissue regeneration and/or wound healing, prior to the administration step. A subject to whom the active ingredient is administered may be a subject who has a skin tissue or organ tissue damage or has received a skin transplant.

Another embodiment provides a pharmaceutical composition for inhibiting Ang2 and/or activating a Tie2 receptor including the anti-Ang2 antibody or an antigen-binding fragment thereof as an active ingredient. Another embodiment provides a method for inhibiting Ang2 and/or activating a Tie2 receptor including administering a pharmaceutically effective amount of the anti-Ang2 antibody or an antigen-binding fragment thereof to a subject. The subject may be in need of Ang2 inhibition and/or Tie2 receptor activation. The Ang2 inhibition and/or Tie2 receptor activation method may further include a step of identifying a subject who is in need of Ang2 inhibition and/or Tie2 receptor activation, prior to the administration step. The anti-Ang2 antibody or an antigen-binding fragment thereof may be in a form of being bound to an antigen Ang2.

Since the function of the anti-Ang2 antibody or an antigen-binding fragment thereof, which is an active ingredient of the above pharmaceutical compositions, is activated by the binding with Ang2, the pharmaceutical compositions may further include Ang2 to enhance the function of the antibody or the antigen-binding fragment thereof. The above methods may further include a step of administering a pharmaceutically effective amount of Ang2 to a subject. The Ang2 may be administered together with the anti-Ang2 antibody or an antigen-binding fragment thereof simultaneously or sequentially in any order.

As described above, the anti-Ang2 antibody or an antigen-binding fragment thereof has a function of inhibiting increase of vascular permeability by inducing vascular normalization, thereby being effectively used in prevention and/or treatment of a disease accompanied with vascular leakage.

Another embodiment provides a pharmaceutical composition for blocking vascular leakage including the anti-Ang2 antibody or an antigen-binding fragment thereof as an active ingredient. Another embodiment provides a method of blocking vascular leakage, including administering the anti-Ang2 antibody or an antigen-binding fragment thereof to a subject in need of blocking vascular leakage. The method may further include a step of identifying the subject who needs to block vascular leakage. Another embodiment provides a use of the anti-Ang2 antibody or an antigen-binding fragment thereof for blocking vascular leakage or for preparing a medicament for blocking vascular leakage. The anti-Ang2 antibody or an antigen-binding fragment thereof may be used in the form of complex where the anti-Ang2 antibody or an antigen-binding fragment thereof is bound to its antigen, Ang2. Since the anti-Ang2 antibody or an antigen-binding fragment thereof in activated by binding with Ang2, the composition may further include Ang2 for enhancing the function of the antibody or an antigen-binding fragment thereof. In addition, the method may further include a step of administering a pharmaceutically effective of Ang2 to a subject.

Another embodiment provides a pharmaceutical composition for preventing and/or treating a disease accompanied by vascular leakage including the anti-Ang2 antibody or an antigen-binding fragment thereof as an active ingredient. Another embodiment provides a method of preventing and/or treating a disease accompanied by vascular leakage, including administering the anti-Ang2 antibody or an antigen-binding fragment thereof to a subject in need of preventing and/or treating a disease accompanied by vascular leakage. The method may further include a step of identifying the subject who needs to prevent and/or treat a disease accompanied by vascular leakage. Another embodiment provides a use of the anti-Ang2 antibody or an antigen-binding fragment thereof for preventing and/or treating a disease accompanied by vascular leakage or for preparing a medicament for preventing and/or treating a disease accompanied by vascular leakage. The anti-Ang2 antibody or an antigen-binding fragment thereof may be used in the form of complex where the anti-Ang2 antibody or an antigen-binding fragment thereof is bound to its antigen, Ang2. Since the anti-Ang2 antibody or an antigen-binding fragment thereof in activated by binding with Ang2, the composition may further include Ang2 for enhancing the function of the antibody or an antigen-binding fragment thereof. In addition, the method may further include a step of administering a pharmaceutically effective of Ang2 to a subject.

Another embodiment provides a pharmaceutical composition for preventing and/or treating a disease accompanied by vascular inflammation including the anti-Ang2 antibody or an antigen-binding fragment thereof as an active ingredient. Another embodiment provides a method of preventing and/or treating a disease accompanied by vascular inflammation, including administering the anti-Ang2 antibody or an antigen-binding fragment thereof to a subject in need of preventing and/or treating a disease accompanied by vascular inflammation. The method may further include a step of identifying the subject who needs to prevent and/or treat a disease accompanied by vascular inflammation. Another embodiment provides a use of the anti-Ang2 antibody or an antigen-binding fragment thereof for preventing and/or treating a disease accompanied by vascular inflammation or for preparing a medicament for preventing and/or treating a disease accompanied by vascular inflammation. The anti-Ang2 antibody or an antigen-binding fragment thereof may be used in the form of complex where the anti-Ang2 antibody or an antigen-binding fragment thereof is bound to its antigen, Ang2. Since the anti-Ang2 antibody or an antigen-binding fragment thereof in activated by binding with Ang2, the composition may further include Ang2 for enhancing the function of the antibody or an antigen-binding fragment thereof. In addition, the method may further include a step of administering a pharmaceutically effective of Ang2 to a subject.

Another embodiment provides a pharmaceutical composition for preventing and/or treating sepsis including the anti-Ang2 antibody or an antigen-binding fragment thereof as an active ingredient. Another embodiment provides a method of preventing and/or treating sepsis, including administering the anti-Ang2 antibody or an antigen-binding fragment thereof to a subject in need of preventing and/or treating sepsis. The method may further include a step of identifying the subject who needs to prevent and/or treat sepsis. Another embodiment provides a use of the anti-Ang2 antibody or an antigen-binding fragment thereof for preventing and/or treating sepsis or for preparing a medicament for preventing and/or treating sepsis. The anti-Ang2 antibody or an antigen-binding fragment thereof may be used in the form of complex where the anti-Ang2 antibody or an antigen-binding fragment thereof is bound to its antigen, Ang2. Since the anti-Ang2 antibody or an antigen-binding fragment thereof in activated by binding with Ang2, the composition may further include Ang2 for enhancing the function of the antibody or an antigen-binding fragment thereof. In addition, the method may further include a step of administering a pharmaceutically effective of Ang2 to a subject.

Another embodiment provides a composition for diagnosing a disease related to angiogenesis and/or increase of vascular permeability and/or decrease of normal blood vessel formation decrease and/or vascular leakage and/or vascular inflammation, including the anti-Ang2 antibody or an antigen-binding fragment thereof. Another embodiment provides a method of diagnosing a disease related to angiogenesis and/or increase of vascular permeability and/or decrease of normal blood vessel formation decrease and/or vascular leakage and/or vascular inflammation, including treating a biological sample derived from a patient with the anti-Ang2 antibody or an antigen-binding fragment thereof, and measuring a level of an antigen-antibody reaction. In this method, when the level of the antigen-antibody reaction in the biological sample is higher than that of a normal sample, the patient from which the biological sample is derived may be determined as having diagnosing a disease related to angiogenesis and/or increase of vascular permeability and/or decrease of normal blood vessel formation decrease and/or vascular leakage and/or vascular inflammation. Therefore, the method may further include treating a normal sample with the anti-Ang2 antibody or an antigen-binding fragment thereof, and measuring a level of an antigen-antibody reaction. Another embodiment provides a use of the anti-Ang2 antibody or an antigen-binding fragment thereof for diagnosing a disease related to angiogenesis and/or increase of vascular permeability and/or decrease of normal blood vessel formation decrease and/or vascular leakage and/or vascular inflammation.

The biological sample may be at least one selected from the group consisting of a cell, a tissue, fluid (e.g., blood, serum, and the like) and the like, derived from a patient to be diagnosed. The biological sample may be separated from a living body. The normal sample may be at least one selected from the group consisting of a cell, a tissue, fluid (e.g., blood, serum, and the like) and the like, derived from a patient having no disease related to angiogenesis, and/or vascular permeability increase and/or normal blood vessel formation decrease. The normal sample may be separated from a living body. The patient may be selected from mammal including primates such as a human, a monkey, and the like, and rodents such as a mouse, a rat, and the like.

The pharmaceutical compositions may further include a pharmaceutically acceptable carrier, and the carrier may be those commonly used in the formulation of drugs, which may be one or more selected from the group consisting of lactose, dextrose, sucrose, sorbitol, mannitol, starch, gum *acacia*, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but is not limited thereto. The pharmaceutical compositions may further include one or more selected from the group consisting of a diluent, an excipient, a lubricant, a wetting agent, a sweetener, a flavor enhancer, an emulsifying agent, a suspension agent, and a preservative.

Pharmaceutically effective amounts of the pharmaceutical compositions, or the antibody or the antigen-binding fragment thereof may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration leads to digestion of proteins or peptides, an active ingredient in the compositions for oral administration must be coated or formulated to prevent digestion in stomach. In addition, the composition may be administered using an optional device that enables an active substance to be delivered to target cells.

The content of the anti-Ang2 antibody or an antigen-binding fragment thereof in the pharmaceutical compositions may be prescribed in a variety of ways, depending on factors such as formulation methods, administration methods, age of subjects, body weight, gender, pathologic conditions, diets, administration time, administration interval, administration route, excretion speed, and reaction sensitivity. For example, a daily dosage of the anti-Ang2 antibody or an antigen-binding fragment thereof may be within the range of 0.001 to 1000 mg/kg, particularly 0.01 to 100 mg/kg, and more particularly 0.1 to 50 mg/kg, but is not limited thereto. The daily dosage may be formulated into a single formulation in a unit dosage form or formulated in suitably divided dosage forms, or it may be manufactured to be contained in a multiple dosage container. The term "pharmaceutically effective amount" as used herein refers to a content or dose of an active ingredient capable of showing desirable pharmacological effects and it may be determined in a variety of ways, depending on factors such as formulation methods, administration methods, age of subjects, body weight, gender, pathologic conditions, diets, administration time, administration interval, administration route, excretion speed, and reaction sensitivity.

The pharmaceutical compositions may be formulated into a form of a solution in oil or an aqueous medium, a suspension, syrup, an emulsifying solution, an extract, powder, granules, a tablet, or a capsule, and may further include a dispersing or a stabilizing agent for the formulation.

In particular, the pharmaceutical compositions including the anti-Ang2 antibody or an antigen-binding fragment thereof may be formulated into an immunoliposome since it contains an antibody or an antigen-binding fragment. A liposome containing an antibody may be prepared using any methods widely known in the art. The immunoliposome may be a lipid composition including phosphatidylcholine, cholesterol, and polyethyleneglycol-derivatized phosphatidylethanolamine, and may be prepared by a reverse phase evaporation method. For example, Fab' fragments of an antibody may be conjugated to the liposome through a disulfide-exchange reaction.

Meanwhile, as the anti-Ang2 antibody or an antigen-binding fragment thereof specifically binds to Ang2, this can be used to detect Ang2, and the presence of the overexpression of Ang2 can be verified through it. Accordingly, another embodiment provides a composition for detecting Ang2 and a composition for diagnosing a disease related to Ang2 overexpression including the anti-Ang2 antibody or an antigen-binding fragment thereof.

In another embodiment, provided is a method for detecting Ang2 including treating a living specimen obtained (or isolated) from a subject with the anti-Ang2 antibody or an antigen-binding fragment thereof; and identifying the presence of an antigen-antibody reaction. Also, there is provided a method of providing information for diagnosis of a disease related to Ang2 overexpression, including treating a living specimen obtained from a subject with the anti-Ang2 antibody or an antigen-binding fragment thereof; and identifying the presence of an antigen-antibody reaction. The method of providing information for the diagnosis may determine a subject to have Ang2 overexpression symptoms, or have Ang2 overexpression related diseases when an antigen-antibody reaction is detected in the step of identifying the presence of an antigen-antibody reaction. The living specimen may be selected from the group consisting of cells, tissues and body fluids obtained (isolated) from a subject.

The step of identifying the presence of the antigen-antibody reaction may be performed using various methods known in the art. For example, it may be measured through an ordinary enzyme reaction, fluorescence, luminescence, and/or radioactivity detection and particularly, it may be measured by a method selected from the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, etc., but is not limited thereto.

The subjects which the pharmaceutical composition or the antibody or the antigen-binding fragment thereof is administered to or is aimed to diagnose may be mammals including primates such as humans and monkeys, or rodents such as rats and mice, or cells, tissues and body fluids isolated therefrom or artificially cultured.

The diseases related to angiogenesis and/or vascular permeability increase and/or Ang2 overexpression may be cancer; cancer metastasis; ocular blood vessel disorders such as retinopathy of prematurity, macular degeneration (e.g., age-related macular degeneration), diabetic retinopathy, neovascular glaucoma, etc.; inflammatory disorders such as psoriasis, asthma, rheumatoid arthritis, pneumonia, chronic inflammation, etc.; infectious disorders (infection); cardiovascular disorders such as hypertension, arteriosclerosis, etc.; renal disease; sepsis; asthma; edema; hereditary hemorrhagic telangiectasia (HHT), etc. The cancer may be those overexpressing Ang2, it may be a solid cancer or a blood cancer, and it may be, but not limited to, selected from the group consisting of squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatocellular cancer, gastric cancer, pancreatic cancer, glioblastoma, cervical cancer, ovarian cancer, liver cancer, bladder cancer, hepatoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, etc.

The diseases related to normal blood vessel formation decrease are diseases that require the induction of normal blood vessel formation and may be selected from the group consisting of ischemic disorders such as myocardial infarction, angina, cerebral infarction, stroke (ischemic stroke), etc., Buerger' disease (thromboangiitis obliterans), avascular necrosis, foot ulcer (e.g., diabetic foot ulcer), erectile dysfunction and so on.

The disease accompanied by vascular leakage may be selected from the group consisting of sepsis, vascular leak syndrome, acute respiratory distress syndrome (ARDS), acute lung injury (ALI), diabetic vascular complications, and the like.

The disease accompanied by vascular inflammation may be selected from the group consisting of sepsis, vascular infection, infectious diseases, and the like.

In particular, sepsis is a disease accompanied by systemic inflammatory response and vascular leakage, and thus, the anti-Ang2 antibody or an antigen-binding fragment thereof having an excellent effect of decreasing inflammation and vascular permeability may be useful in preventing and/or treating sepsis.

In the treatment of a disease related to angiogenesis and/or increase of vascular permeability and/or overexpression of Ang2, a disease accompanied by vascular leakage, a disease accompanied by vascular inflammation, for example sepsis, the anti-Ang2 antibody or an antigen-binding fragment thereof may be co-administered with a pre-existing drug for treatment of a disease related to angiogenesis and/or increase of vascular permeability and/or overexpression of Ang2, a disease accompanied by vascular leakage, a disease accompanied by vascular inflammation, for example sepsis, thereby exhibiting synergistic treatment effects. Therefore, the anti-Ang2 antibody or an antigen-binding fragment thereof may be effectively used as a pharmaceutical composition for combination therapy of preventing and/or treating a disease related to angiogenesis and/or increase of vascular permeability and/or overexpression of Ang2, a disease accompanied by vascular leakage, a disease accompanied by vascular inflammation, for example sepsis.

In this aspect, the pharmaceutical composition for preventing and/or treating a disease related to angiogenesis and/or increase of vascular permeability and/or overexpression of Ang2, a disease accompanied by vascular leakage, a disease accompanied by vascular inflammation, for example sepsis, may further include a drug for treatment of a disease related to angiogenesis and/or increase of vascular permeability and/or overexpression of Ang2, a disease accompanied by vascular leakage, a disease accompanied by vascular inflammation, for example sepsis. Another embodiment provides a composition for combination therapy including the anti-Ang2 antibody or an antigen-binding fragment thereof and at least one selected from the group consisting of drugs for preventing and/or treating a disease related to angiogenesis and/or increase of vascular permeability and/or overexpression of Ang2, a disease accompanied by vascular leakage, a disease accompanied by vascular inflammation, or sepsis. The drug may be at least one selected from the group consisting of all compounds, antibodies, genes (for example, antisense oligonucleotide, siRNA, shRNA, microRNA, and the like), aptamers, therapeutic cells, radiopharmaceutical drugs, which have the effect of prevention and/or treatment of a disease related to angiogenesis and/or increase of vascular permeability and/or overexpression of Ang2, a disease accompanied by vascular leakage, a disease accompanied by vascular inflammation, for example sepsis, and/or reduce or improvement of symptoms. For example, the drug may be at least one selected from the group consisting of antibiotics, drotrecogin alpha, corticosteroid, vasopressin, and the like, but not be limited thereto.

Another embodiment provides a complex in which the anti-Ang2 antibody or an antigen-binding fragment thereof, Ang2, and Tie2 receptor are bound (e.g., a complex including anti-Ang2 antibody or an antigen-binding fragment thereof, Ang2, and Tie2 receptor, wherein the anti-Ang2 antibody or an antigen-binding fragment thereof is specifically bound to Ang2, and the Ang2 is bound to the Tie2 receptor, and the anti-Ang2 antibody or an antigen-binding fragment thereof is bound to the Tie2 receptor via Ang2). The complex may be present inside the body or present in a cell isolated from the body. Also, the antibody in the complex may form a dimer with another antibody in an adjacent complex, thereby clustering two or more complexes, to form a cluster including two or more complexes (see Example 8). Such action is related to the Tie2 receptor activation function of the anti-Ang2 antibody. The complex can be used to monitor the action of the anti-Ang2 antibody, i.e., the presence of Ang2 inhibition and/or Tie2 receptor activation, or simply used to inhibit Ang2 and/or to activate Tie2 receptor.

Another embodiment provides a method for screening a candidate drug for preventing and/or treating a disease related to Ang2 overexpression, angiogenesis, increase of vascular permeability, and/or a decrease in normal blood vessel formation by identifying the complex formation, and/or the presence of Ang2 inhibition and/or Tie2 receptor activation.

In one embodiment, the screening method may comprise or consist essentially of:

contacting a candidate compound to a specimen containing Ang2 and a Tie2 receptor; and identifying the formation of a complex in which the candidate compound, Ang2, and the Tie2 receptor are bound.

The step of identifying the formation of a complex in which the candidate compound, Ang2, and the Tie2 receptor are bound may be performed by identifying the presence of a complex in which the candidate compound, Ang2, and the Tie2 receptor are bound, or identifying the presence of binding between the candidate compound and Ang2 and the presence of binding between Ang2 and the Tie2 receptor. The screening method may further include a step of identifying Ang2 inhibition and/or Tie2 receptor activation, before or after the step of identifying the formation of a complex in which the candidate compound, Ang2, and the Tie2 receptor are bound, or simultaneously therewith.

In the above screening method, when the formation of a complex in which the candidate compound, Ang2, and the Tie2 receptor are bound is identified, in other words, in case that the presence of a complex in which the candidate compound, Ang2, and the Tie2 receptor are bound is identified, or in case that binding between the candidate compound and Ang2 and binding between Ang2 and the Tie2 receptor are identified, the candidate compound can be determined to be a candidate for preventing and/or treating a disease related to Ang2 overexpression, angiogenesis, increase of vascular permeability, and/or decrease of normal blood vessel formation.

In another embodiment, the screening method may comprise or consist essentially of:

contacting a candidate compound to a specimen containing Ang2 and a Tie2 receptor; and identifying Ang2 inhibition and/or Tie2 receptor activation (i.e., Ang2 inhibition, Tie2 receptor activation, or a combination thereof). In this screening method, when Ang2 inhibition and/or Tie2 receptor activation is identified, the candidate compound can be determined to be a candidate for preventing and/or treating a disease related to Ang2 overexpression, angiogenesis, increase of vascular permeability, and/or decrease of normal blood vessel formation. The inhibition (degradation) of Ang2 may be identified by measuring the levels of Ang2 before/after the same specimen is treated with Ang2, or measuring the levels of Ang2 after the same specimen is divided into a treatment group and a non-treatment group, and then comparing the levels of Ang2 before/after the treatment of the candidate compound or in the treatment group and the non-treatment group. When the level of Ang2 after the treatment of the candidate compound or in the treatment group is decreased, in comparison with the pre-treatment of the candidate compound or the non-treatment group, Ang2 may be determined to be inhibited. Also, the activation of Tie2 receptor may be identified by measuring the phosphorylation degrees of the Tie2 receptor and/or the phosphorylation degree of at least one protein involved in the downstream signaling of the Tie2 receptor (for example, Akt, eNOS, 42/44, etc.) before/after the same specimen is treated with the candidate compound, or measuring them after the same specimen is divided into a treatment group and a non-treatment group, and then comparing the phosphorylation degrees of the proteins before/after the treatment of the candidate compound or in the treatment group and the non-treatment group. When the phosphorylation degree after the treatment of the candidate compound or in the treatment group is increased, in comparison with the pre-treatment of the candidate compound or the non-treatment group, the Tie2 receptor may be determined to be activated. Also, the activation of the Tie2 receptor may be determined by identifying the presence of the intracellular internalization of the Tie2 receptor.

In another embodiment, the screening method may comprise or consist essentially of:

contacting a candidate compound to a specimen containing Ang2 and a Tie2 receptor; and identifying i) the formation of the complex in which the candidate compound, Ang2, and the Tie2 receptor are bound, ii) Tie2 receptor activation, or both of Ang2 inhibition and Tie2 receptor activation, or iii) both of i) and ii). A detailed matter of the formation of a complex, Ang2 inhibition, and Tie2 receptor are described above. In the screening method, identification of (i) or (ii), or both, may indicate that the candidate compound is a candidate drug for preventing or treating a disease related to Ang2 overexpression, angiogenesis, increase of vascular permeability, or a decrease in normal blood vessel formation. Therefore, the screening method may further comprise, after the step of identifying, a step of determining the candidate compound as a candidate for preventing and/or treating a disease related to Ang2 overexpression, angiogenesis, increase of vascular permeability and/or a decrease in normal blood vessel formation when i) the formation of the complex in which the candidate compound, Ang2, and the Tie2 receptor are bound, ii) Tie2 receptor activation, or both of Ang2 inhibition and Tie2 receptor activation, or iii) both of i) and ii) is identified (confirmed).

The identification of the complex formation, the measurement of Ang2 level, the measurement of Tie2 phosphorylation degree, the measurement of the phosphorylation degree of the proteins involved in downstream signaling, and/or the identification of the intracellular internalization of Tie2 receptor may be performed using various methods known in the art and for example, they may be measured through an ordinary enzyme reaction, fluorescence, luminescence, and/or radioactivity detection and particularly, they may be measured by a method selected from the group consisting of immunochromatography, immunohistochemistry, enzyme linked immunosorbent assay (ELISA), radioimmunoassay (RIA), enzyme immunoassay (EIA), fluorescence immunoassay (FIA), luminescence immunoassay (LIA), western blotting, etc., but is not limited thereto.

The candidate compounds may be one or more selected from the group consisting of various artificially-synthesized or natural compounds, polypeptides, oligopeptides, peptide or protein scaffolds (for example, antibody, peptibody, nanobody, etc.), polynucleotides, oligonucleotides, antisense-RNA, shRNA (short hairpin RNA), siRNA (small interference RNA), aptamers, natural product extracts and so on.

The specimen containing Ang2 and Tie2 receptor may be cells or tissues isolated from a living body (e.g., a mammal including human) or artificially cultured, and they may intrinsically contain (express) Ang2 and the Tie2 receptor, may be treated with Ang2 and/or the Tie2 receptor, or may be manipulated to express Ang2 and/or the Tie2 receptor.

Previously, there were attempts to inhibit angiogenesis by Ang2 by inhibiting binding between Ang2 and its receptor Tie2, but an antibody which specifically binds to Ang2 to induce the intracellular internalization and degradation of Ang2 and at the same time, maintains a binding ability with Ang2 and Tie2 receptor to form an antibody-Ang2-Tie2 receptor complex, thereby activating the Tie2 receptor has not been known so far. Under such circumstances, the invention proposes a novel method capable of inhibiting angiogenesis by Ang2 and reducing vascular permeability by suggesting an antibody which inhibits Ang2 and at the same time activates the Tie2 receptor to accelerate its downstream signaling. Also, the antibody proposed in the invention is anticipated to be applicable to diagnose and treat abnormal blood vessel formation-related disorders other than cancer and/or disorders caused by vascular permeability increase. The antibody can be utilized for combination therapy with chemical medicines and other anticancer drugs, and is expected to be employed for antibody fragments, bi- or multi-specific antibodies, protein scaffolds, etc. using Ang2 specific recognition activity.

Hereafter, the present invention will be described in detail by examples. They are intended merely to illustrate the invention and are not construed to restrict the invention. It will be obvious to those skilled in the pertinent art that the following examples may be modified within the scope of not deviating from the essential gist of the invention.

EXAMPLE 1

Preparation of Anti-Ang2 Antibody

A human Ang2 protein (R&D systems; 623-AN-025/CF) was administered to 5-week-old BALB/c mice along with an adjuvant to induce an immune response and then, hybridomas that produce an individual anti-Ang2 antibody were prepared according to the known methods described in the paper written by Schwaber, et al (Schwaber, J and Cohen, E. P., "Human×Mouse Somatic Cell Hybrid Clones Secreting Immunoglobulins of Both Parental Types," Nature, 244 (1973), 444-447).

More specifically, to obtain immunized mice necessary for developing hybridoma cell lines, 100 ug (microgram) of human Ang2 protein (R&D Systems) mixed with the same amount of a complete Freund's adjuvant was administered via an intraperitoneal injection to each of five 4~6-week-old BALB/c mice (Japan SLC, Inc.). After two weeks, the antigen (half the previously injected amount) mixed with an incomplete Freund's adjuvant using the same method as described above was administered to each mouse via an intraperitoneal injection. After one additional week, a final boosting was performed and three days later, blood was collected from the tail of each mouse to obtain serum, which was then diluted at 1/1000 with PBS and subjected to an ELISA to verify that the titer of an antibody recognizing Ang2 was increased. From the results, mice in which a sufficient amount of the antibody was obtained were selected, and a cell fusion process was performed on the selected mice.

Three days before the cell fusion experiment, a mixture of 50 ug of PBS and 100 ug of human Ang2 protein (R&D systems) was administered via an intraperitoneal injection to BALB/c mice (Japan SLC, Inc.), and after each immunized mouse was anesthetized, its spleen located on the left side of the body was extracted. The extracted spleen was ground with a mesh to isolate cells, which were mixed with a culture medium (DMEM, Hyclon) to prepare a spleen cell suspension. The suspension was centrifuged to collect a cell layer. The obtained $1\times10^8$ spleen cells were mixed with $1\times10^7$ myeloma cells (Sp2/0), and the mixture was centrifuged to precipitate the cells. The centrifuged precipitate was slowly dispersed, treated with 1 ml of 45% polyethylene glycol (PEG 1500) contained in a culture medium (DMEM), and maintained at 37° C. for one minute before adding 1 ml of a culture medium (DMEM). Subsequently, 10 ml of the culture medium (DMEM) was added for 1 minute to the resultant, which was incubated in a water bath at 37° C. for 5 minutes and then re-centrifuged after the total volume was adjusted to 50 ml. The resulting cell precipitate was re-suspended in an isolation medium (HAT medium) at a concentration of 1~2×10⁵/ml, and the resultant suspension was distributed at 0.1 ml to the each well of a 96-well plate, which was then incubated in a carbon dioxide incubator at 37° C. to prepare the hybridoma cell groups.

EXAMPLE 2

Manufacture of Anti-Ang2 Antibody 2.1. Selection of Anti-Ang2 Antibody Producing Clone and Purification of Antibody The above obtained individual antibody producing hybridomas were screened using a typical ELISA format to select hybridomas which produce 95 anti-Ang2 monoclonal antibodies among the hybridomas differentiated from their mother hybridomas, based on their binding potential with Ang2.

More specifically, to select the hybridoma cells that specifically react only to Ang2 protein among the hybridoma cell groups prepared in Example 1 above, an ELISA assay method using a human Ang2 protein as an antigen was used for screening.

Human Ang-2 protein was added at 100 ng per well to a microtiter plate to be adhered to the surface of the plate, and unreacted antigens were removed by washing. 50 microliters of the hybridoma cell culture obtained in Example 1 above was added to each well to react for 1 hour and then, the wells were sufficiently washed with phosphate buffered saline-TWEEN 20 (PBST) solution to remove unreacted culture solution. Goat anti-mouse IgG-horseradish peroxidase (goat anti-mouse IgG-HRP) was added thereto, a reaction was allowed to occur at a room temperature for 1 hour and then, washing was sufficiently performed with the TBST solution. Subsequently, substrate solution (OPD) of peroxidase was added to each well to react, and the reaction degree was measured by the absorption at 450 nm using an ELISA reader to repeatedly select hybridoma cell lines that secret antibodies having specifically high binding affinity only to human Ang2 protein. A limiting dilution was performed on the hybridoma cell lines obtained through repetitive selection to obtain final 58 clones of hybridoma cell lines producing monoclonal antibodies. The thus prepared hybridomas were deposited in the Korean Cell Line Bank located at Yongon-dong, Chongno-gu, Seoul, South Korea, as of Apr. 23, 2013 and received accession number KCLRF-BP-00295.

Each hybridoma obtained above was cultured in DMEM (Dulbeco's Modified Eagle's Medium) and then, the culture solutions were collected and subjected to Protein G-affinity chromatography method to purify anti-Ang2 monoclonal antibodies produced from each hybridoma.

First, the hybridoma cells cultured in 50 ml of culture medium (DMEM) containing 10% (v/v) FBS were centrifuged to obtain a cell precipitate, which was washed at least twice with 20 ml of PBS to remove the FBS. The cell precipitate was re-suspended in 50 ml of the culture medium (DMEM) and then incubated in a carbon dioxide incubator at 37° C. for 3 days. Subsequently, the cell culture was centrifuged to remove the antibody-producing cells, and the culture medium including the secreted antibodies was isolated and then, stored at 4° C. or used directly. Antibodies were purified from 50 to 300 ml of the culture medium using an AKTA purification device (GE Healthcare) equipped with an affinity column (protein G agarose column; Pharmacia, USA). The purified antibodies were stored for subsequent use after replacing the supernatant with PBS using a filter for protein aggregation (Amicon). One of the antibodies obtained from each hybridoma above was named 10D6.

The binding affinity of the above antibody to human Ang-2 protein was measured by an SPR method using a BIAcore T100 (GE Healthcare). The SPR method uses refractive index change of light which passes a sensor chip according to the state of materials coated onto the sensor chip, and if an antigen or an antibody is flowed onto a chip coated with the antigen or antibody, it causes changes in refractive index due to their binding and Kd values are thus calculated from the measured values.

First, anti-His antibody was immobilized on a CM5 sensor chip (GE healthcare) up to 8,000 RU levels using a pH 5.0 acetate solution and an amine coupling kit (GE Healthcare). 6 μg/ml of a recombinant hAng-2 (C-His, R&D Systems) protein was flowed onto the chip to be captured at 100 to 200 RU levels. The antibody obtained in Example 2 above was diluted serially to twice each time starting from 100 nM concentration and it was each flowed onto the chip to allow it to be bound to (on), dissociated from (off), and regenerated (using 10 mM NaOH solution) from the antigen captured on the sensor chip, thereby to measure antigen-antibody affinity. With regard to hAng2, such experiments were conducted, and the results are as shown in the following Table 3.

TABLE 3

| Antibody Name | hAng2 (Kd) |
| --- | --- |
| SAIT-ANG2-AB-m10D6 | 8.0 nM |

2.2. Gene Cloning of Anti-Ang2 Antibody

A whole RNA was obtained using RNeasy mini kit (Qiagen) from the antibody-producing hybridoma (2×10⁶ cells) obtained from Example 2.1 above. Then, by using this as a template, only the gene sequence of the heavy chain and light chain variable regions of the monoclonal antibody to be produced in the hybridoma was amplified using a OneStep RT-PCR kit (Qiagen), a Mouse Ig-Primer Set (Novagen), and a thermocycler (GeneAmp PCR System 9700, Applied Biosystem) under the following conditions: 5 min. at 94° C.; [30 min. at 50° C., 15 min. at 95° C.], [1 min. at 94° C., 1 min. at 50° C., 2 min. at 72° C.]×35 cycles; 6 min. at 72° C.; cooling to 4° C.

The PCR products obtained from each reaction were subjected to a direct DNA sequencing to obtain the CDR, heavy chain variable regions and light chain variable regions of the antibody, and nucleotide sequences encoding them, and the obtained results are set forth in the following Tables 4 to 7.

TABLE 4

| | Heavy Chain CDR Sequence | | |
| --- | --- | --- | --- |
| Antibody Name | CDRH1-KABAT | CDRH2-KABAT | CDRH3-KABAT |
| SAIT-ANG2-AB-m10D6 | SDYAWN (SEQ ID NO: 1) | YINYSGNTDYNPSLKS (SEQ ID NO: 2) | GNFEGAMDY (SEQ ID NO: 3) |

TABLE 5

| Antibody Name | Light Chain CDR Amino Acid Sequence | | |
|---|---|---|---|
| | CDRL1-KABAT | CDRL2-KABAT | CDRL3-KABAT |
| SAIT-ANG2-AB-m10D6 | KASQSVSNDVA (SEQ ID NO: 4) | YASNRYP (SEQ ID NO: 5) | QQDYSSPWT (SEQ ID NO: 6) |

TABLE 6

| Antibody Name | Heavy Chain Variable Region Sequence |
|---|---|
| SAIT-ANG2-AB-m10D6 | DVQLQESGPGLVKPSQSLSLTCTVTGYSITSDYAWNWIRQFPGNK LEWMGYINYSGNTDYNPSLKSRSSITRDTSKNQFFLQLNSVTTGD TATYYCARGNFEGAMDYWGQGTSVTVSS (SEQ ID NO: 7)<br><br>GATGTGCAGCTTCAGGAGTCGGGACCTGACCTGGTGAAACCTT CTCAGTCTCTGTCCCTCACCTGCACTGTCACTGGCTACTCAATC ACCAGTGATTATGCCTGGAACTGGATCCGGCAGTTTCCAGGAA ACAAACTGGAGTGGATGGGCTACATAAACTACAGTGGTAACAC TGACTACAACCCATCTCTCAAAAGTCGAAGCTCTATCACTCGAG ACACATCCAAGAACCAGTTCTTCCTGCAGTTGAATTCTGTGACT ACTGGGGACACAGCCACATATTACTGTGCAAGAGGTAACTTCG AAGGTGCTATGGACTACTGGGGTCAAGGAACCTCAGTCACCGT CTCCTCA (SEQ ID NO: 8) |

TABLE 7

| Antibody Name | Light Chain Variable Region Sequence |
|---|---|
| SAIT-ANG2-AB-m10D6 | SIVMTQTPKFLLVSAGDRVTITCKASQSVSNDVAWYQQKPGQSP KLLIYYASNRYPGVPDRFTGSGYGTDFTFTISTVQAEDLAVYFCQQDYSSPWTFGGGTKLEIK (SEQ ID NO: 9)<br><br>agtattgtgatgacccagactcccaaattcctgcttgtatcagcaggagacagggttaccataa cctgcaaggccagtcagagtgtgagtaatgatgtagcttggtaccaacagaagccagggca gtctcctaaactgctgatatactatgcatccaatcgctaccctggagtccctgatcgcttcactgg cagtggatatgggacggatttcactttcaccatcagcactgtgcaggctgaagacctggcagtt tatttctgtcagcaggattatagctctccgtggacgttcggtggaggcaccaagctggaaatca aa (SEQ ID NO: 10) |

(In above Tables 6 and 7, underlined bold letters are CDR1, CDR2, and CDR3 in sequence)

EXAMPLE 3

Competition ELISA Assay of Antibody 10D6 Against Ang2-Tie2 Binding

Ang2-Tie2 binding competition ELISA was conducted using the antibody binding to Ang-2 prepared in Example 2-1 above.

More specifically, MaxiSorp™ flat-bottom plate (Nunc) of 96-well was coated with hTie2-Fc (R&D Systems) which is a protein bound with 4 ug (microgram)/ml of Fc of human IgG1. After that, the plate was washed five times with 0.05% (v/v) Tween-20-containing PBS (phosphate buffer saline) and then blocked with 1% (v/v) BSA (bovine serum albumin; Sigma)-containing PBS at a room temperature for 2 hour.

For Ang2:Tie2 competition ELISA, each anti-Ang2 antibody obtained in Example 2 was placed at various concentrations of 400 nM to 0.001 nM into each well coated with the hTie-2/Fc fusion protein along with 1% (v/v) BSA and 400 ng/ml of a FLAG-tagged hAng-2 and then, the plate was allowed to react at a room temperature for 2 hours and washed five times with PBST. After that, an anti-FLAG antibody (Sigma) conjugated with HRP diluted in 1% (v/v) BSA-containing PBS at a ratio of 1:5,000 (v/v) was added in an amount of 100 ul (microliter) to each well to react at a room temperature for 1 hour and then, the plate was washed five times with PBST. Lastly, 100 ul (microliter) of TMB substrate (Cell Signaling) was added to each well of the plate to induce color development for 3 min. and then, the reaction was ceased by the addition of 100 ul of Stop solution (Cell Signaling) and OD450 values were measured on a plate reader (Molecular Devices).

For comparison, the same test was carried out using 4H10 which is an anti-Ang2 antibody inhibiting Ang2-Tie2 binding. The 4H10 is an antibody having the following heavy chain variable region and light chain variable region.

Heavy chain variable region (SEQ ID NO: 12):
EVQLLESGGGLVQPGGSLRLSCAASGFTFSSYDMSWVRQAPGKGLEWVSL

ISPDSSSIYYADSVKGRFTISRDNSKNTLYLQMNSLRAEDTAVYYCAKDL

ISFWRGGFDYWGQGTLVTVSS

Light chain variable region (SEQ ID NO: 13)
QSVLTQPPSASGTPGQRVTISCSGSSSNIGSNYVNWYQQLPGTAPKLLIY

ADSNRPSGVPDRFSGSKSGTSASLAISGLRSEDEADYYCGSWDYSLSGYV

FGGGTKLTVLG

An inhibitory degree (%) against Ang2-Tie2 binding is shown in FIG. 1. As seen in FIG. 1, unlike 4H10 which is an anti-Ang2 antibody inhibiting Ang2-Tie2 binding, antibody 10D6 did not inhibit binding between Ang2-Tie2 receptor.

EXAMPLE 4

Verification of Antigen Recognizing Site (Epitope) of Ang2 Antibody

To verify the epitope (or specific binding site) of the anti-Ang2 antibody prepared in Example 2, an ELISA was performed using a recombinant protein where a receptor binding domain (RBD) of Ang2 protein in the form of being tagged with Flag was mutated by artificial means.

Each well of a 96-well MaxiSorp™ flat-bottom plate (Nunc) was coated with 50 ul (microliter) of 1000 nM antibody. Then, the plate was washed five times with 0.05% (v/v) Tween-20-containing PBS (PBST) and blocked with 1% (v/v) BSA-containing PBS at a room temperature for 2 hours. 250 ng of each mutant Ang2 protein obtained by substituting S417, Q418, P419, N421, I434, D448, A449, P452, Y460, N467, K468, or F469 residue of Ang2 protein tagged with a FLAG sequence (Sigma) at its N-terminal with alanine was added to each well of the plate, which was then allowed to react at a room temperature for 2 hours.

The plate was washed five times with 0.05% (v/v) Tween-20 containing PBS, reacted with an anti-FLAG antibody (SIGMA) conjugated with HRP which was diluted in 1% (v/v) BSA-containing PBS at a ratio of 1:5,000 (v/v) at a room temperature for 1 hour, and washed five times with 0.1% (v/v) Tween-20-containing PBS.

Finally, 50 ul of TMB substrates (Cell signaling) was added to each well of the plate to induce color development at a room temperature for 3 min. and the reaction was ceased by the addition of 50 ul of Stop solution (Cell signaling) and then, OD450 values were measured on a plate reader (Molecular Devices). By comparing binding affinities with mutated Ang2 to those of unmutated Ang2, each epitope of Ang2 antibodies was identified. The thus obtained measurement results of the binding affinities (%) with mutant Ang2 against the binding affinity with the native Ang2 are shown in the following Table 8.

cultured for 10 min. After washed once again with PBS, the cultured cells were treated with a mixture prepared by mixing the anti-Ang2 antibody (10D6) having various concentrations (600~0.06 nM) with 40 nM of Ang2 protein (R&D systems) and letting them stand for 20 min. and further cultured for 10 min. The cells were washed using PBS, treated with 400 ul of a lysis buffer (Roche), collected to a tube to be dissolved at 4° C. for 30 min. and then, centrifuged at 13,000 rpm for 15 min. to measure a supernatant using Nanodrop.

1 ug of Tie2 antibody (R&D system) was added to 0.8 mg of a cell lysate, which was then overnight reacted at 4° C. and then subjected to immunoprecipitation by the addition of protein A bead (GE Healthcare) thereto. The thus obtained reactant was centrifuged at 13,000 rpm for 15 min. to obtain a pellet, which was washed two to three times with a lysis buffer (Roche), added to a sample buffer (Invitrogen) mixed with a reducing agent, and boiled at 95° C. for 5 min., and then, applied to NuPAGE Novex 4-12% Bis-Tris gel (Invitrogen) and transferred onto Nitrocellulose membrane (Invitrogen).

To see the presence of the phosphorylation of Tie2, the membranes were blocked with PBST mixed with 3% (v/v) skim milk (Sigma) for 30 min. and identified using an HRP-conjugated anti-phospho tyrosine antibody (Millipore). For Tie2 identification, the blots were reacted in a stripping buffer (Thermo) for 15 min, then blocked again and identified using an Tie2 antibody (Santa cruz).

Figure 2A:
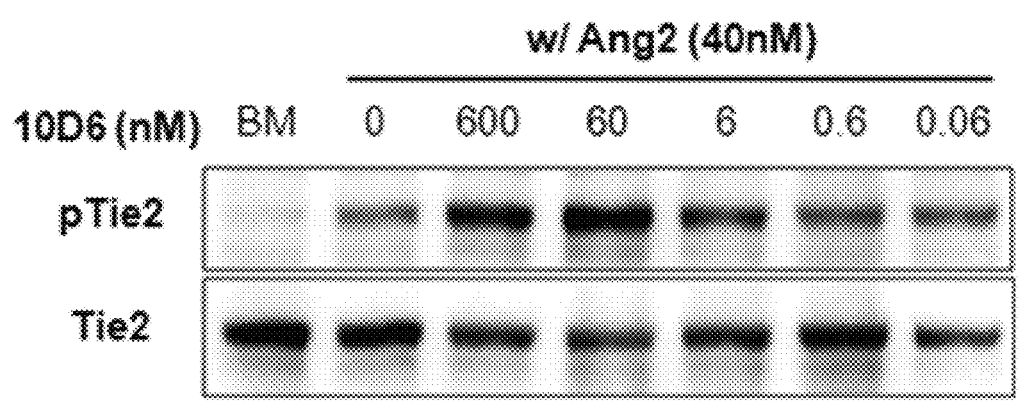
FIG. 2A is an annotated photograph of the immunoblotting results showing the level of Tie2 receptor and a phosphorylated Tie2 receptor according to the concentration of an anti-Ang2 antibody.

The thus obtained results are shown in FIG. 2A. As shown in FIG. 2A, when antibody 10D6 was added together with Ang2, the phosphorylation of Tie2 was more strongly induced at every antibody concentration range tested than the case in which Ang2 was treated alone.

In addition, referring to the above method, when 60 nM of antibody 10D6 and Ang2 were treated, the phosphorylation level of Tie2 was measured and compared with the case of treating a control antibody (anti-Ang2 antibody (Regeneron) which has MOA of inhibiting binding between

TABLE 8

| | Loop 1 | | | | | Loop 2 | | | Loop 3 | | | Loop 4 |
|---|---|---|---|---|---|---|---|---|---|---|---|---|
| | 417 | 418 | 419 | 421 | 434 | 448 | 449 | 452 | 460 | 467 | 468 | 469 |
| 10D6 | 101.17 | 38.94 | 41.08 | 109.09 | 109.49 | 104.55 | 97.86 | 102.15 | 103.15 | 106.84 | 110.27 | 108.79 |

EXAMPLE 5

Phosphorylation Induction of Tie2 Receptor by Antibody 10D6

As Ang2 induces a change in vascular endothelial cells by binding to a Tie-2 receptor expressed in the vascular endothelial cells to induce the phosphorylation of the receptor and activate it, a test for analyzing an influence of the anti-Ang2 antibody on Tie2 phosphorylation was conducted using a cell-based assay.

Figure 2B:
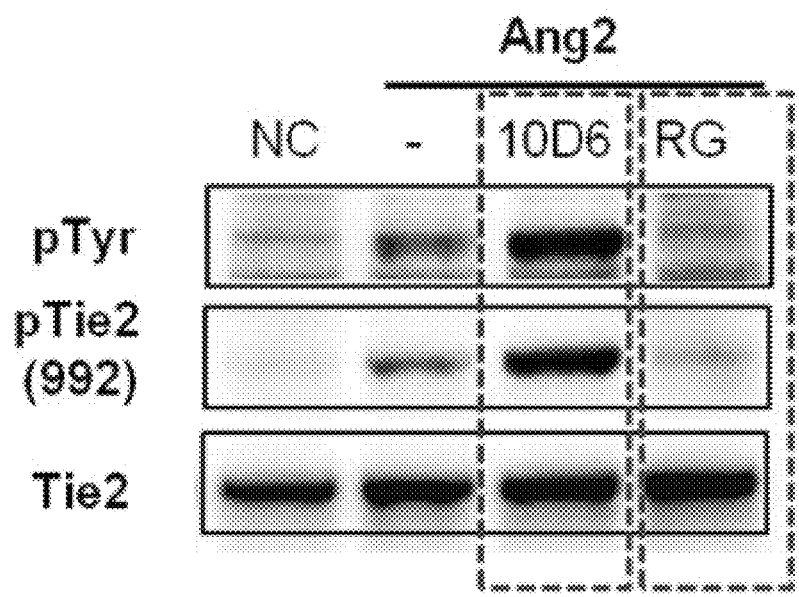
FIG. 2B is an annotated photograph of the immunoblotting results showing the level of Tie2 receptor and a phosphorylated Tie2 receptor according to the concentration of an anti-Ang2 antibody compared to that of a control antibody (RG).

For this, HUVEC (ATCC) cells (1×10$^6$) were cultured in a 100 mm culture dish using EGM-2 (Lonza) media at 37° C. and when they reached 80~90% confluency, the media were replaced with serum-free media and cultured at 37° C. for 6 to 16 hours. The dish was washed once with PBS and after the replacement with 1 nM sodium orthovanadate (Sigma)-mixed serum free media (Lonza), they were further Ang2 and Tie2; represented as 'RG antibody'). The obtained immunoblotting results are shown in FIG. 2B. After treating with the antibody (10D6 or RG), the blot band density of pTyr and Tie2 was measured using ImageJ software and pTyr/Tie2 ratio was calculated. The obtained result is demonstrated in FIG. 2C.

Figure 2C:
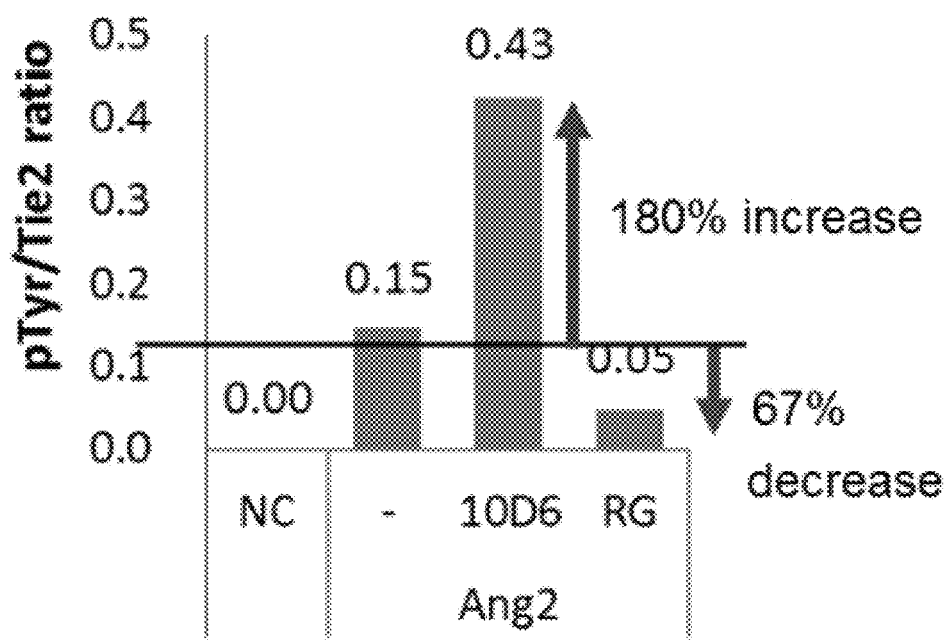
FIG. 2C is a graph showing a ratio of phosphorylated Tyr in Tie2 receptor.

In FIGS. 2B and 2C, "NC" represents Tie2 phosphorylation results in a group which is not treated with antibody nor Ang2. As shown in FIGS. 2B and 2C, when treated with antibody 10D6, Tie2 phosphorylation level is increased by 180% compared to the case that Ang2 is treated only without treating with antibody; whereas, when treated with control antibody RG, Tie2 phosphorylation level is decreased by 67% compared to the case that Ang2 is treated only without treating with antibody, indicating that antibody 10D6 has about 8.6-fold higher Tie2 phosphorylation effect than control antibody.

EXAMPLE 6

Activation Induction of Tie2 Signaling by Antibody 10D6

To see whether antibody 10D6 induces the activation of the downstream signaling of a Tie2 receptor as well as the activation of the Tie2 receptor itself, the phosphorylation degrees of proteins participating in the downstream signaling when Ang2 alone or Ang2 and antibody 10D6 was treated were tested using immune blotting. To compare the activation degrees of the downstream signaling, the same test was conducted with regard to a group in which Ang1 (R&D systems), and Ang2 (R&D systems) and an anti-Ang2 antibody (RG antibody; control antibody having MOA inhibiting Ang2-Tie2 binding, Regeneron Co.) were treated together.

Specifically, HUVEC (ATCC) cells ($1 \times 10^6$) were cultured in a 6-well culture dish using EGM-2 (Lonza) media at 37° C. and when they reached 80~90% confluency, the media were replaced with serum-free media (Lonza) and cultured at 37° C. for 6 to 16 hours. The dish was washed once with PBS, and the cultured cells were treated with a mixture prepared by mixing 60 nM of the Ang2 antibody (10D6) with 40 nM of Ang2 protein (R&D systems) and letting them stand for 20 min. and further cultured for 30 min. For comparison, groups in which Ang1 (R&D systems) 4 nM, Ang2 (R&D systems) 40 nM, and Ang2 (R&D systems) 40 nM+anti-Ang2 antibody (Regeneron) 60 nM were treated respectively were prepared.

The cells were washed using PBS, treated with a lysis buffer (Roche), collected to a tube to be dissolved at 4° C. for 30 min. and then, centrifuged at 13,000 rpm for 15 min. to measure a supernatant. A sample buffer (Invitrogen) mixed with a reducing agent was added to 25 ug of a cell lysate, which was boiled at 95° C. for 5 min., and then, applied to NuPAGE Novex 4-12% Bis-Tris gel (Invitrogen) and transferred onto Nitrocellulose membrane (Invitrogen).

To see the presence of the phosphorylation of Akt, eNOS and 42/44 involved in the downstream signaling, the blots were blocked with PBST mixed with 3% (v/v) skim milk (Sigma) for 30 min. and then treated with an anti-pAkt antibody, anti-p-eNOS antibody, and anti-p-42/44 antibody (all of them; cell signaling). The blots were reacted in a stripping buffer (Thermo) for 15 min. and then blocked again to identify Akt, eNOS, and 42/44 using an anti-Akt antibody, anti-eNOS antibody, and anti-42/44 antibody (all of them; cell signaling).

Figure 3A:
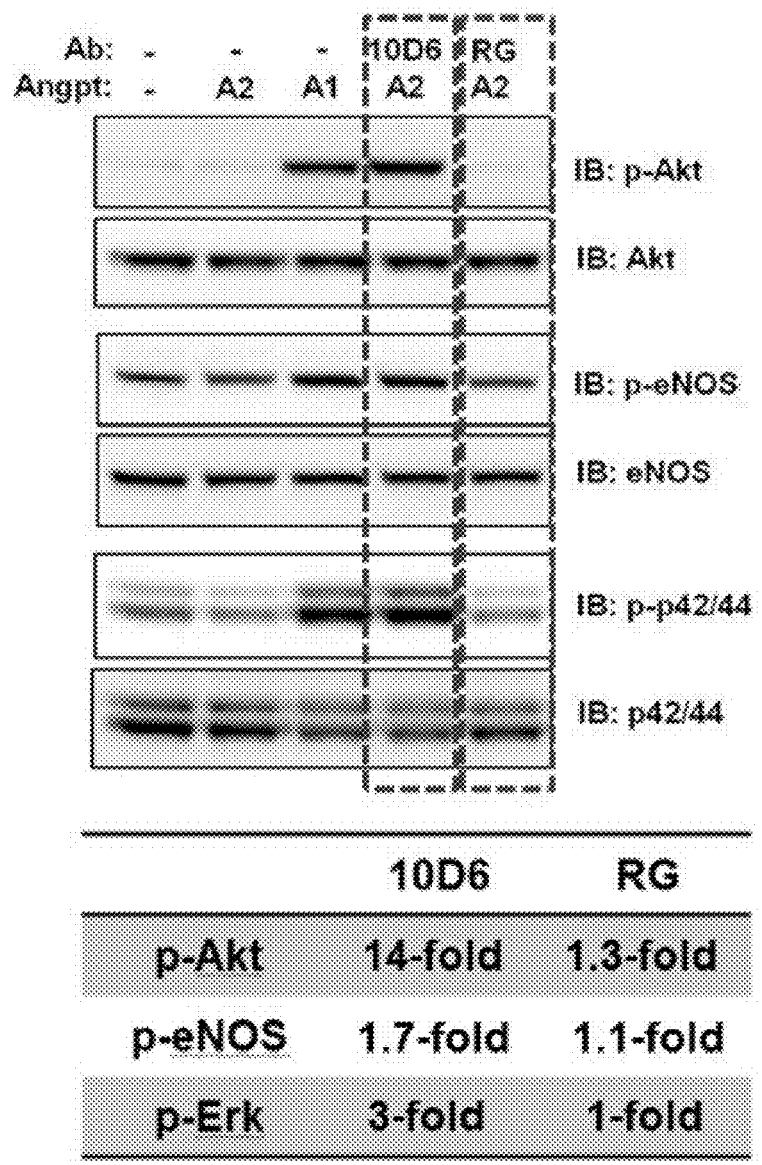
FIG. 3A is an annotated photograph of the immunoblotting results showing the phosphorylation of proteins involved in the downstream signaling of a Tie2 receptor by an anti-Ang2 antibody.

The thus obtained results are shown in FIG. 3A. As seen in FIG. 3A, in the Ang1 sole-treatment group and the Ang2 and 10D6 co-treatment group, downstream signaling was strongly induced in comparison with the Ang2 sole-treatment group and the Ang2 and RG antibody co-treatment group, and the effects in the Ang2 and antibody 10D6 co-treatment group was at least equal to those in the Ang1 sole-treatment group.

In addition, the phosphorylation of Tie2 receptor and a protein (Akt) which participates in downstream signaling of Tie2 by treating anti-Ang2 antibody was measured in animal model (in vivo). More particularly, 5 mg/kg of antibody was injected alone or together with 20 ug of Ang2 into tail vein of 7-8 week old C57BL6 mouse, and 1 hour after, lung tissue was removed. The obtained lung tissue was subjected to homogenization lysis using lysis buffer (Roche) and Fast-Prep kit (MP biomedicals). Activities of Tie2 and Akt in the obtained tissue lysate were measured by the above-described method.

Figure 3B:
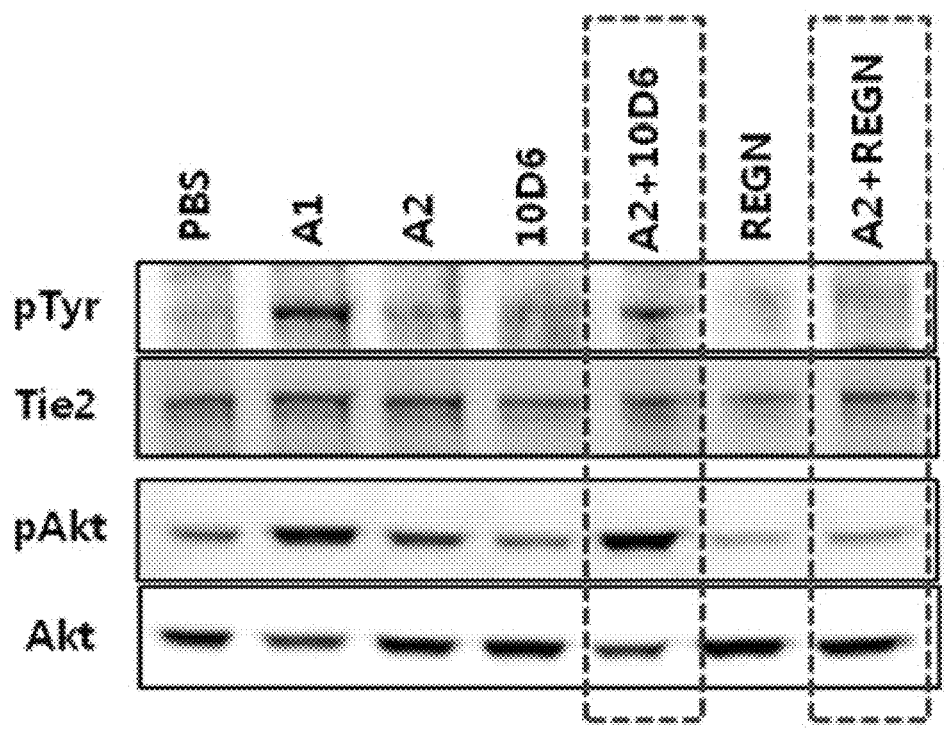
FIG. 3B is an annotated photograph of the immunoblotting results showing the phosphorylation of Tie2 receptor and a protein (Akt) involved in the downstream signaling of a Tie2 receptor by an anti-Ang2 antibody.
Figure 3C:
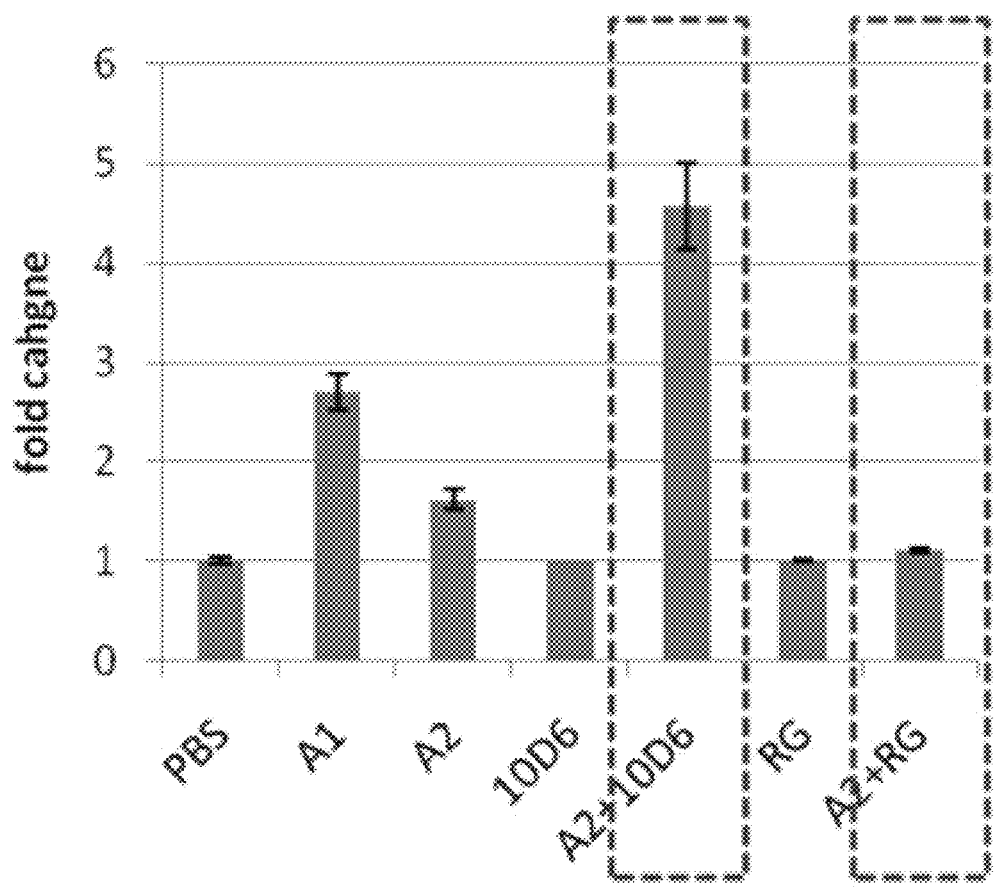
FIG. 3C is a graph showing the results of 3B as numerical values.

The obtained results are demonstrated in FIGS. 3B and 3C. In FIGS. 3B and 3C, "REGN" or "RG" represents a control antibody (anti-Ang2 antibody of Regeneron). As shown in FIGS. 3B and 3C, even in vivo experimentation, antibody 10D6 exhibits considerable effect of phosphorylating Tie2 and a protein, Akt, participating in downstream signaling of Tie2.

EXAMPLE 7

ELISA Assay for Identifying Formation of 10D6-Ang2-Tie2 Complex

As it was confirmed that 10D6 anti-Ang2 antibody activates Tie2 signaling without inhibiting Ang2-Tie2 binding, an ELISA was conducted to see whether a complex between the antibody and Ang2:Tie2 receptor is formed.

A 96-well MaxiSorp™ flat-bottom plate (Nunc) was coated with 4 ug/ml of Tie2-Fc (R&D systems) or BSA (Sigma). Then, the plate was washed five times with 0.05% (v/v) Tween-20-containing PBS (Phosphate Buffer Saline) and blocked with 1% (v/v) BSA (Bovine serum albumin; Sigma)-containing PBS at a room temperature for 2 hours. 0.25 ug/ml of Ang2 and 2 ug/ml of antibody 10D6 were added to each well of the plate, which was allowed to react at a room temperature for 2 hours and then washed five times with PBST. After that, an anti-mouse IgG antibody (Sigma) conjugated with HRP diluted in 1% (v/v) BSA-containing PBS at a ratio of 1:5,000 (v/v) was added in an amount of 100 ul to each well to react at a room temperature for 1 hour and then, the plate was washed five times with PBST. Lastly, 100 ul (microliter) of TMB substrate (Cell Signaling) was added to each well of the plate to induce color development for 3 min. and then, the reaction was ceased by the addition of 100 ul of Stop solution (Cell Signaling) and OD450 values were measured on a plate reader (Molecular Devices).

The thus obtained results are shown in FIG. 4. As seen in FIG. 4, it was confirmed that antibody 10D6 formed a complex by binding to Ang2 which was bound to Tie2.

EXAMPLE 8

Activation Induction via Tie2 Receptor Clustering by Dimerization of Antibody 10D6

To see whether the activation of a Tie2 receptor is resulted from the dimerization of antibody 10D6, Fab fragments of antibody 10D6 were purified and then used for this experiment. The Fab fragments were obtained from antibody 10D6 using an Fab Preparation Kit (Pierce). As a digestion buffer, PBS containing 20 mM EDTA and 20 mM L-Cysteine was used, and the antibody was separated into Fab and Fc by the treatment with an immobilized papain at a room temperature for 2 hours. The Fc fragments were removed from the reaction solution using MabSelectSuRe column (GE Healthcare) to isolate and purify pure Fab fragments only.

HUVEC (ATCC) cells ($1 \times 10^6$) were cultured in a 100 mm culture dish using EGM-2 (Lonza) media at 37° C. and when they reached 80~90% confluency, the media were replaced with serum-free media (Lonza) and cultured at 37° C. for 6 to 16 hours. The dish was washed once with PBS and after the replacement with 1 nM sodium orthovanadate (Sigma)-mixed serum free media (Lonza), they were further cultured for 10 min. After washed once with PBS, the cultured cells were treated with a mixture prepared by mixing 60 nM of 10D6 Ang2 antibody or 10D6 Fab with 40 nM of Ang2 protein (R&D systems) and letting them stand for 20 min. and further cultured for 10 min. The cells were washed using PBS, treated with 400 ul of a lysis buffer (Roche), collected to a tube to be dissolved at 4° C. for 30 min. and then, centrifuged at 13,000 rpm for 15 min. to measure a supernatant using Nanodrop.

1 ug of Tie2 antibody (R&D system) was added to 0.8 mg of a cell lysate, which was then overnight reacted at 4° C. and then subjected to immunoprecipitation by the addition of protein A bead (GE Healthcare) thereto. The thus obtained reactant was centrifuged at 13,000 rpm for 15 min. to obtain a pellet, which was washed two to three times with a lysis buffer (Roche), added to a sample buffer (Invitrogen) mixed with a reducing agent, and boiled at 95° C. for 5 min., and then, applied to NuPAGE Novex 4-12% Bis-Tris gel (Invitrogen) and transferred onto Nitrocellulose membrane (Invitrogen).

To see the presence of the phosphorylation of Tie2, the membranes were blocked with PBST mixed with 3% (v/v) skim milk (Sigma) for 30 min. and identified using an HRP-conjugated anti-phospho tyrosine antibody (Millipore). For Tie2 identification, the blots were reacted in a stripping buffer (Thermo) for 15 min, then blocked again and identified using an Tie2 antibody (Santa cruz).

To see the presence of the phosphorylation of Akt, eNOS and 42/44 involved in the downstream signaling, the blots were blocked with PBST mixed with 3% (v/v) skim milk (Sigma) for 30 min. and then treated with an anti-pAkt antibody, anti-p-eNOS antibody, and anti-p-42/44 antibody (all of them; cell signaling). The blots were reacted in a stripping buffer (Thermo) for 15 min. and then blocked again to identify Akt, and 42/44 using an anti-Akt antibody, and anti-42/44 antibody (all of them; cell signaling).

The thus obtained results are shown in FIG. 5. As seen in FIG. 5, when antibody 10D6 was added together with Ang2, the phosphorylation of Tie2 and Akt and 42/44 occurred whereas when the 10D6 Fab was treated, activation was not observed. Therefore, it was confirmed that the Tie2 receptor was clustered by the dimerization of the 10D6 antibodies and strongly phosphorylated.

EXAMPLE 9

Internalization of Tie2 Receptor by Antibody 10D6

HUVEC (ATCC) cells ($1 \times 10^6$) were cultured in m-slide 8 wells (#80826, ibidi) for 24 hours and then subjected to serum starvation in serum-free EBM-2 media (Lonza) for 3 hours. 200 ng/ml of Ang1 (R&D systems) or 2 ug/ml of Ang2 (R&D systems) and 10 ug/ml of antibody 10D6 were each diluted in EBM-2 media and then, the cells were treated with them and incubated according to time specified in the picture. The cells fixed with 4% formaldehyde (Sigma) was dyed first with an anti-Tie2 antibody (R&D systems) and then subjected to a secondary dye with an anti-goat Alexa 555 antibody (red, Life technology) and an anti-mouse Alexa 488 antibody (green, Life technology). The dyed cells were treated with Vectashield mounting medium with DAPI (Vector labs) and then observed using a confocal laser scanning microscopy (Carl Zeiss).

Figure 6A:
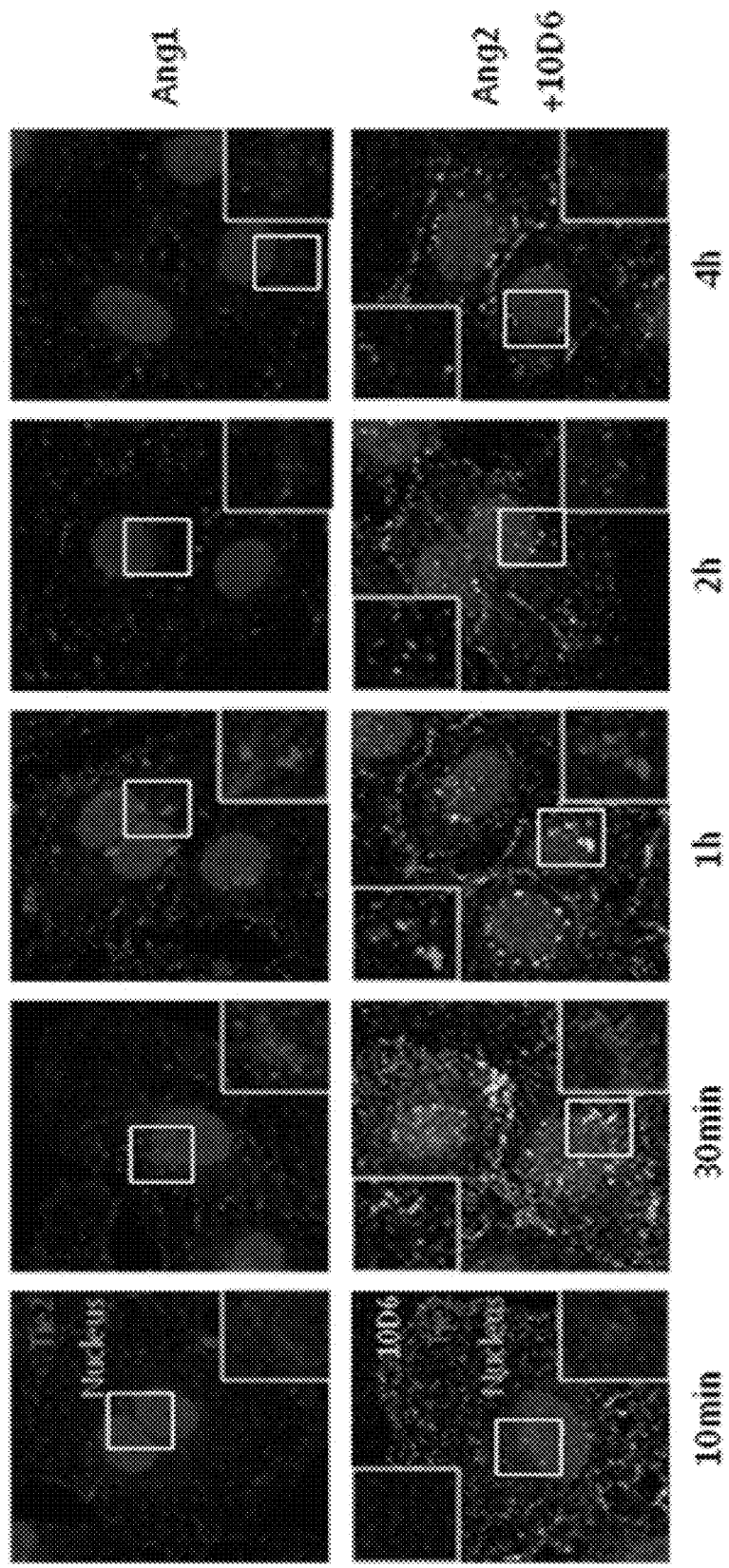
FIGS. 6A and 6B provide a series of fluorescent images showing Ang1 and an anti-Ang2 antibody lead to similar intracellular internalization of a Tie2 receptor.
Figure 6B:
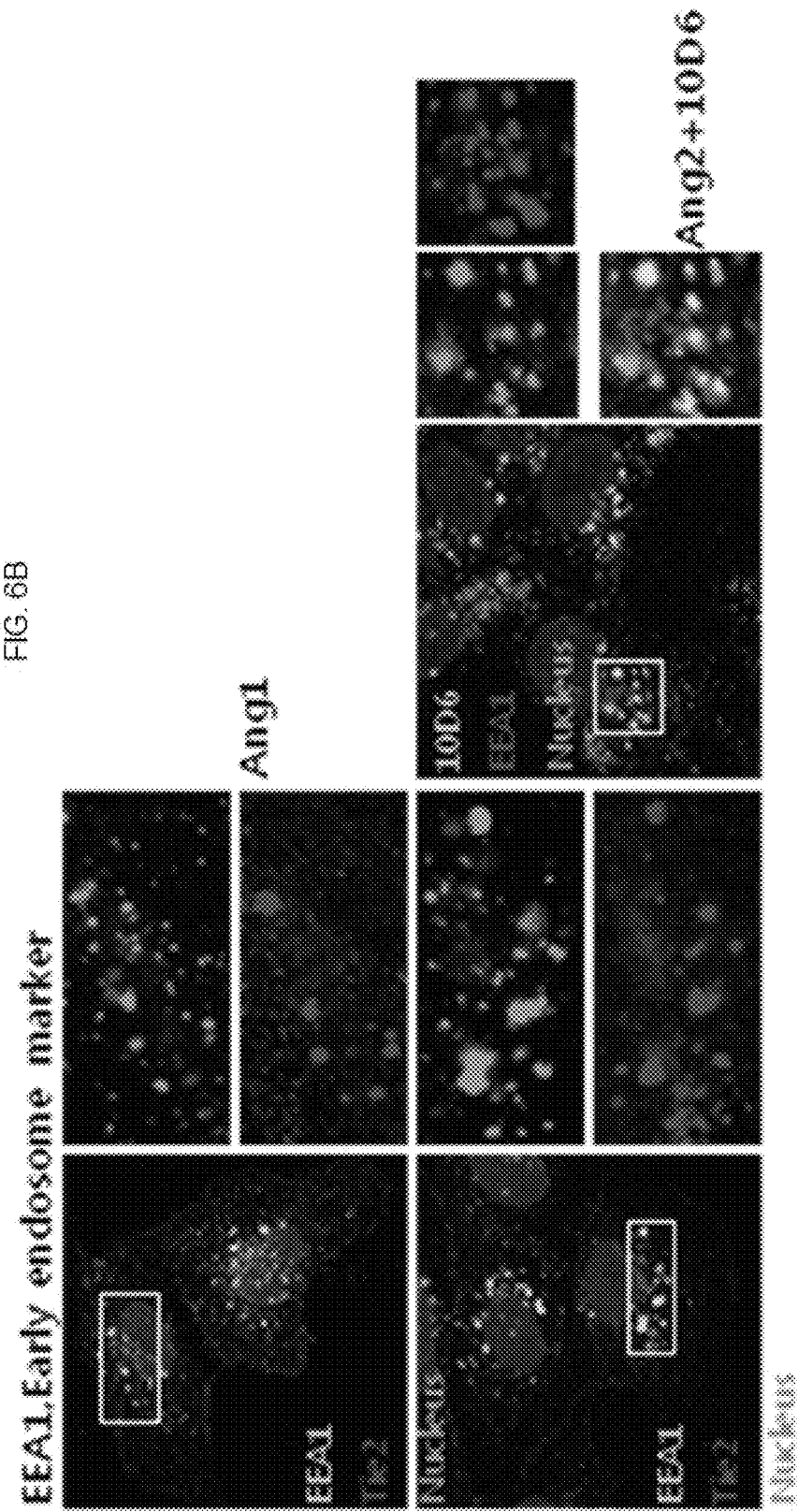

The results are shown in FIG. 6A (red: Tie2, blue: nucleus, green; 10D6) and 6B. As seen in FIG. 6A, when Ang2 and antibody 10D6 were treated, the internalization of the Tie2 receptor started from 30 min., like Tie2 endocytosis occurring when treated with Ang1 (dots in the expanded pictures). Also, it was confirmed that the internalized Tie2 and antibody 10D6 were located in an early endosome which is an intracellular organelle, through anti-EEA1 antibody (Cell Signaling) dye in FIG. 6B.

EXAMPLE 10

Cell Growth and Mobility Increase by Antibody 10D6

The measurement assay of the proliferation of vascular and lymphatic endothelial cells was conducted using a BrdU assay kit (Roche) Cell. Vascular endothelial cells of P3~P8 (HUVEC, ATCC) or lymphatic endothelial cells (Lonza) were placed in a collagen-coated 96-well plate (BD Bioscience) at 3000~5000 cells/well and cultured in EGM-2 media (Lonza) for 16~24 hours. A mixture of 2 ug/ml of Ang2 (R&D systems) and 10 ug/ml of antibody 10D6 in 2% EBM media was added to the 96-well plate washed with PBS, which was then cultured for 3 days.

For efficiency comparison, an anti-Ang2 antibody (MedImmune Co.) was used. For a BrdU assay, 10 ul of BrdU solution diluted at 1:1,000 was added to each well of the plate to label the cells. The cells were cultured for 1 hour and after the removal of the culture solution, 100 ul of Fixation/Denaturation solution (Roche) was added to each well and then, removed after 30-min wait. An anti-BrdU antibody (Roche) conjugated with peroxidase was diluted in a dilution buffer (Roche) at 1:100, added to each well to react for 1 hour and then, washed four times using a washing buffer (Roche). 100 ul of a TMB substrate was added thereto to react and then, absorption was measured at 450 nm using a Microplate reader (Perkin Elmer).

The thus obtained results are shown in FIG. 7. As seen in FIG. 7, the growth of cells was increased in the group in which Ang2 was added together with antibody 10D6 in both vascular endothelial cells and lymphatic endothelial cells, and in the case of MEDI antibody, the growth of the cells by Ang2 was decreased.

Also, the measurement of the mobility of lymphatic endothelial cells was conducted using xCelligence RTCA (Realtime cell analyzer; GE Healthcare). The RTCA is a non-invasive cell monitoring system by measuring impedance in realtime to identify the change of a cell. To perform a cell migration assay, a CIM-plate16 (GE Healthcare) with a lower chamber and an upper chamber was used wherein microelectrodes for measuring impedance are arranged in the upper chamber and if the cells seeded into the chamber migrate through fine holes, the migration degree of the cells can be identified through their adhesion to the microelectrodes, and it was referred to as migration index. The lymphatic endothelial cells (P5-7; Lonza) which grew up in EGM-2 media (Lonza) were cultured in 1% FBS-added EBM media for 6 hours. 2 ug/ml of Ang2 and antibody 10D6 in 2% FBS-added EBM media were added to each well of the lower chamber of the CIM-plate 16, which was assembled with the upper chamber coated with fibronectin (Sigma). For efficiency comparison, an anti-Ang2 antibody (MedImmune Co.) was used. 30 ul of serum-free EBM media was each added to the upper chamber and then, for equilibration between the plate and media, while being placed in an incubator for 1 hour, the CIM-plate was installed on a device station in the incubator and then, background values were measured. The lymphatic endothelial cells re-suspended with serum-free media were seeded in an amount of 60,000 cells/well, allowed to settle down for 15 min. and then, installed on the device to measure cell migration in real time. The cell migration degree was shown as slope (1/hr).

Figure 8:
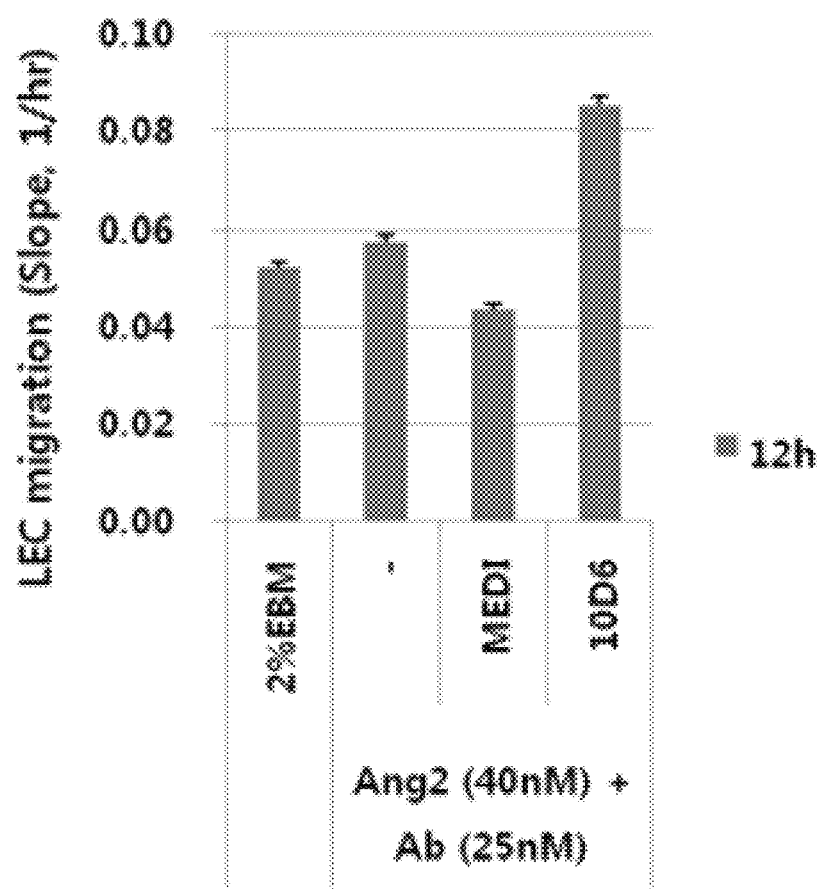
FIG. 8 is a graph showing the migration of lymphatic endothelial cells when treated with an anti-Ang2 antibody.

The thus obtained results are shown in FIG. 8. As seen in FIG. 8, while the migration of the lymphatic endothelial cells to which Ang2 was added together with antibody 10D6 was increased, the migration of the cells by Ang2 was inhibited in the case of MEDI antibody.

EXAMPLE 11

Cell Permeability Suppression by Antibody 10D6

To see the cell permeability suppression effects of antibody 10D6, in vitro vascular permeability assay kit (Millipore) was employed. HUVEC (ATCC) cells ($5 \times 10^4$) were added to a collagen-coated transwell and cultured for 2 days to prepare a confluent monolayer. It was treated with 200 ng/ml of Ang2 or 200 ng/ml of Ang1 (R&D systems) alone, or 200 ng/ml of Ang2 and 1 ug/ml of antibody 10D6, pre-incubated for 30 min. and then, treated with 100 ng/ml of LPS (Lipopolysaccharide; Sigma) or 100 ng/ml TNF-a (R&D systems) to induce the permeability of HUVEC monolayer. LPS or TNF-a weakens binding between HUVEC cells to form a gap therebetween, thereby increasing the migration of materials in the HUVEC monolayer. After 6-hour incubation for the LPS treatment group and 22-hour incubation for the TNF-a group, the upper chamber was treated with FITC-dextran (Millipore) and incubated for 18 min. The fluorescence of FITC-dextran migrated to the lower chamber was measured at 485/535 nm (Ex/Em) setting using an Envision 2104 multilabel Reader (Perkinelmer).

Figure 9:
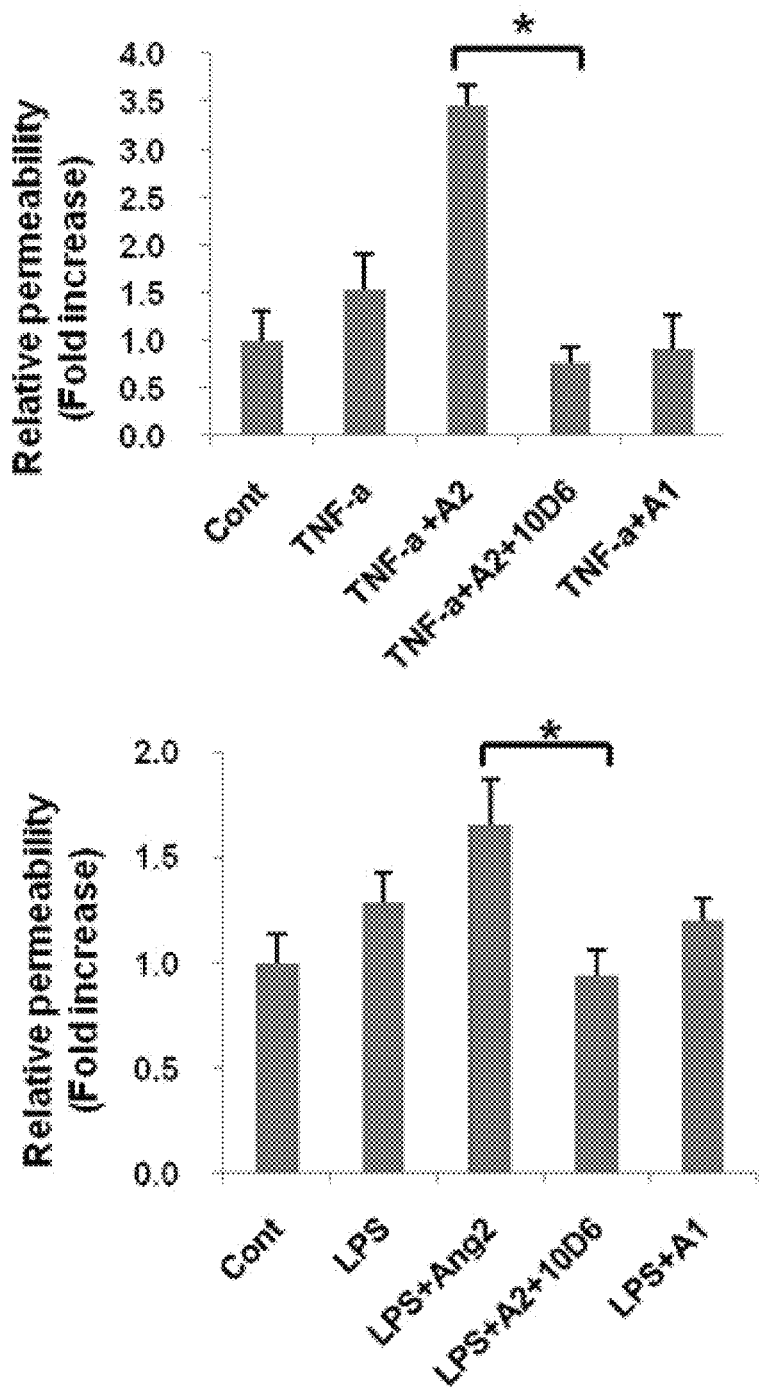
FIG. 9 is a graph showing inhibition of cell permeability induced by TNF or LPS when treated with Ang1 or Ang2 antibody.

The thus obtained results are shown in FIG. 9. FIG. 9 is a graph showing the strength of fluorescence measured above as relative folds, referring to the vascular permeability induced by LPS or TNF-a. Through the results, it was confirmed that the vascular permeability increased by LPS or TNF-a was decreased to the control level in the Ang1 sole-treatment group and in the Ang2 and 10D6 co-treatment group.

EXAMPLE 12

Anti-Inflammatory Effect by Antibody 10D6

To see anti-inflammatory effects by antibody 10D6, HUVEC (ATCC) cells ($4 \times 10^5$) were treated with Ang2 alone or Ang2 together with antibody 10D6, and a group in which Ang1 and Ang2 (R&D systems) and Regeneron Co. antibody (RG antibody) were co-treated was included as a control group. HUVEC cells were treated with 0.2 ug/ml of Ang1, 0.1 ug/ml of Ang2, or 0.1 ug/ml of Ang2 and 0.5 ug/ml of antibody, respectively and after 30-min. pre-incubation, they were treated with 100 ng/ml of LPS (Sigma) to induce inflammatory response and incubated for 5 hours.

The degree of the inflammatory response was identified by measuring the mRNA expression degree of an inflammatory adhesion substance (ICAM-1, E-selectin). The cells were washed using PBS, RNA was extracted using RNeasy Mini kit (Qiagen), and among them, 2 ug of RNA was synthesized into cDNA using Transcriptor First Strand cDNA synthesis kit (Roche). qPCR reaction was performed using RT2 SYBR™ Green Mastermix (Qiagen) and Light-Cycler™ 480 Real-Time PCR System (Roche). As an internal control for calibrating the amount of RNA in a sample, HPRT1 was used, and qPCR complied with the following procedures with regard to all the primers.

Step 1:95° C., 10 min; Step 2 (45 cycles): Step 2-1: 95° C., 15 sec; Step 2-2: 60° C., 1 min; Step 3: 65° C., 15 sec; Step 4: 95° C., continuous (every 20° C.); Step 6: 40° C., 10 sec.

The primer sequences used in qPCR are set forth in the following Table 9.

Step 1: 95° C., 10 min; Step 2 (45 cycles): Step 2-1: 95° C., 15 sec; Step 2-2: 60° C., 1 min; Step 3: 65° C., 15 sec; Step 4: 95° C., continuous (every 20° C.); Step 6: 40° C., 10 sec.

The primer sequences used in qPCR are summarized in Table 9 as follows:

TABLE 9

| Representative Gene | | PCR primer sequence (5'->3') | |
|---|---|---|---|
| Public ID | Symbol | sense | antisense |
| NM_000201.2 | ICAM-1 | ccttcctcaccgtgtactgg | aacctcagcctcgctatgg |
| NM_000450.2 | E-selectin | accagcccaggttgaatg | ggttggacaaggctgtgc |
| NM_000194.2 | HPRT1 | tgaccttgatttattttgcatacc | cgagcaagacgttcagtcct |

Figure 10:
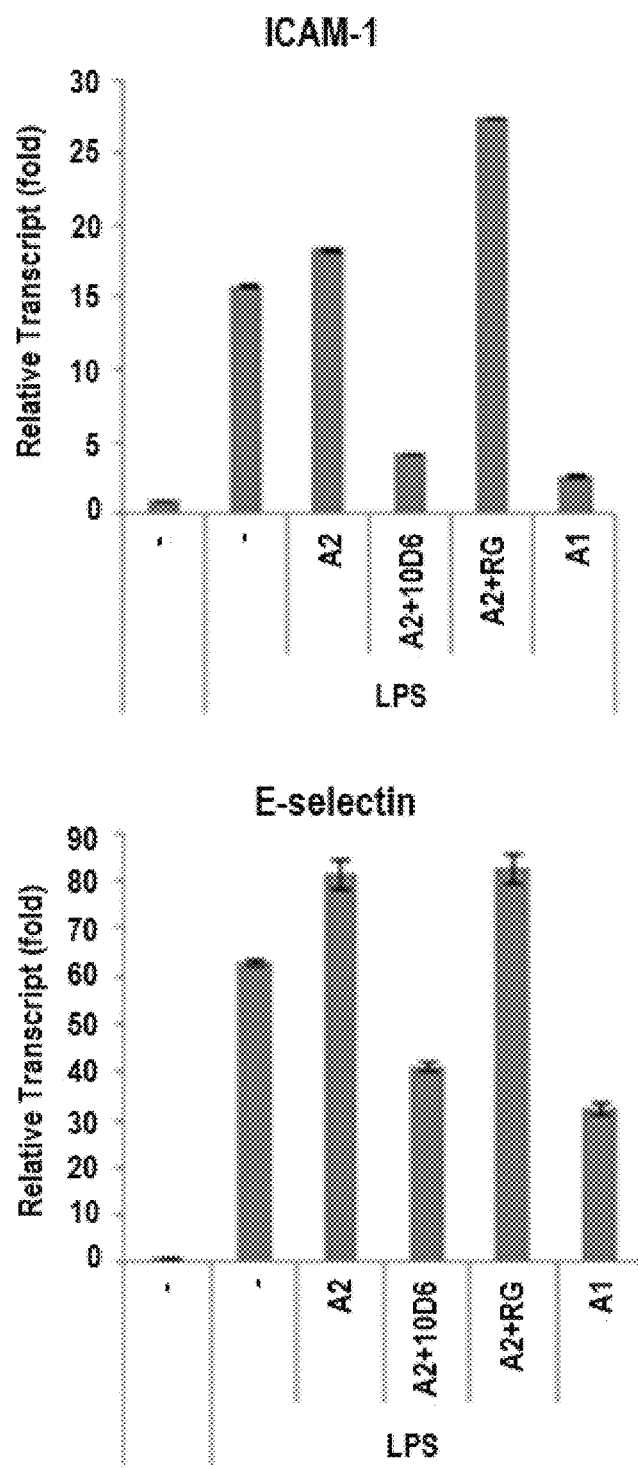
FIG. 10 is a graph showing the mRNA expression of inflammation-related cell adhesion substances (ICAM-1, E-selectin) induced by LPS stimulation when treated with Ang1 or Ang2 antibody.

The relative expression amounts of ICAM-1 and E-selectin measured above are shown in FIG. 10. As seen in FIG. 10, the expression of ICAM-1 and E-selectin induced by LPS were remarkably suppressed in the Ang1 sole-treatment group and in the Ang2 and antibody 10D6 co-treatment group.

Meanwhile, if the expression of inflammatory adhesion substances (ICAM-1, E-selectin, etc.) of vascular endothelial cells is increased, binding between the inflammatory cells and the vascular endothelial cells are accelerated and inflammatory response is thus induced. To confirm this, an experiment for measuring binding between inflammatory cells HL-60 (ATCC) and HUVEC was conducted.

HUVEC cells ($4 \times 10^5$) were cultured in a 24-mutiwell plate and treated with 0.1 ug/ml of Ang2 alone or 0.1 ug/ml of Ang2 together with 0.5 ug/ml of antibody 10D6, and a group in which 0.2 ug/ml of Ang1, and 0.1 ug/ml of Ang2 (R&D systems) and 0.5 ug/ml of Regeneron Co. antibody (RG antibody) were co-treated was included as a control group. As above, the HUVEC cells were treated with Angiopoietin and antibody and after 30-min. pre-incubation, they were treated with 1 ng/ml of TNF-a (eBioscience) to induce inflammatory response and incubated for 2 hours and 30 min.

After the HUVEC cells were washed with complete media (Lonza), HL-60 cells dyed with Calcein-AM (BD bioscience) solution were added at the amount of $2.5 \times 10^5$ cells to each well and incubated for 1 hour. To remove the HL-60 cells not bound to the HUVEC cells, the cells were washed three times using PBS and treated with a lysis buffer (0.1% SDS, 50 mM Tris.HCl, pH 8.0). The obtained lysate was transported to a 96-well plate, and fluorescence strengths derived from the HL-60 cells were measured at 485/535 nm (Ex/Em) setting using an Envision 2104 multilabel Reader (Perkin Elmer).

Figure 11:
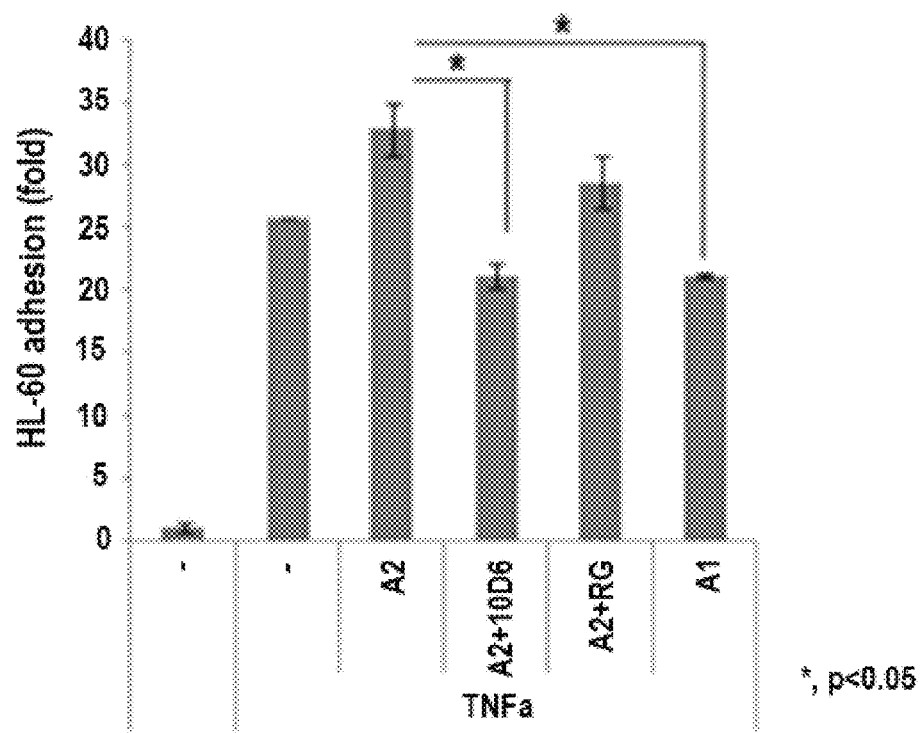
FIG. 11 is a graph showing the strengths of fluorescence obtained from inflammatory cells when treated with an anti-Ang2 antibody as relative folds, and it shows the number of the inflammatory cells adhered to vascular endothelial cells.

The thus obtained results are shown in FIG. 11. The graph of FIG. 11 illustrates the strengths of fluorescence measured above as relative folds and it is proportional to the number of the HL-60 cells adhered to the HUVEC cells. Through the results, binding between HUVEC cells and HL-60 cells induced by TNF-a was remarkably suppressed in the Ang1 sole-treatment group and in the Ang2 and antibody 10D6 co-treatment group.

EXAMPLE 13

Colo205 Tumor Growth Inhibitory Effect of Anti-Ang-2 Antibody

To see the tumor growth inhibitory effects of Ang-2 antibody, a colorectal cancer xenograft model using a human colorectal cancer cell line Colo205 (ATCC) was employed.

The Colo205 cell line was cultured using 10% FBS (Gibco)-added RPMI-1640 (Gibco) media. $5 \times 10^5$ of Colo205 cell line were re-suspended in 100 ul of serum-free media and then injected into anesthetic 4~5-week-old BALB/c nude mice (Shanghai SLAC Laboratory Animal Co. Ltd.) via a subcutaneous injection using 1~2% isoflurane. When the size of tumors reached 100~200 mm$^3$, anti-Ang-2 antibody (10D6) was injected at the concentration of 10 mg/kg via an intraperitoneal injection twice a week and the size of the tumors was measured.

The size of tumor (V) was calculated using the following formula:

$$V=(length \times width^2)/2$$

Figure 12:
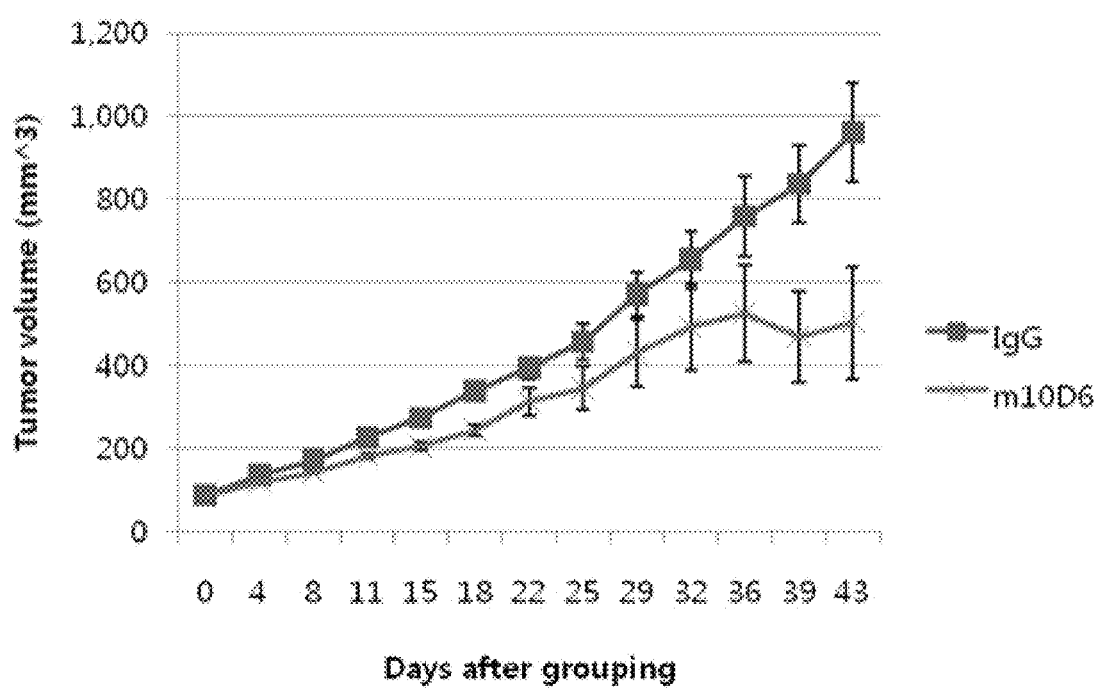
FIG. 12 is a graph showing tumor volume in a Colo205 tumor model when treated with an anti-Ang2 antibody.

The thus obtained results are shown in FIG. 12. The X-axis of FIG. 12 indicates days on which the antibody was treated, as days after grouping. As in FIG. 12, antibody 10D6 inhibited the growth of colorectal cancer.

EXAMPLE 14

Effects of Increasing Survival Rate of LPS-Induced Sepsis Animal Model by Antibody 10D6

Survival rate of an animal model treated with antibody 10D6 was measured, wherein the animal model is a mouse having sepsis accompanied by increase of blood Ang2 concentration, systemic inflammation, and vascular leakage, which is induced by intraperitoneal injection of LPS (Lipopolysaccharide; Sigma), in order to confirm the possibility of antibody 10D6 as a drug for treating sepsis.

5 mg/kg of antibody 10D6 was intraperitoneally injected into adult C57BL/6 mouse (Jackson Laboratory, 6~8 weeks, male). For comparison, animal models which are subjected to intraperitoneal injection of 5 mg/kg of each of antibody of Regeneron Inc. (RE GN), Enbrel (TNF-a blocker; Amgen), Avastin (VEGF-A blocker; Genentech), and a control animal model which is subjected to intraperitoneal injection of 5 mg/kg of PBS, were used. After 1 hour from injection, 15 mg/kg of LPS(Sigma) was intraperitoneally injected into each animal model, to induce sepsis, and survival rate of the animal models was recorded with time for 5 days, to confirm the effect of prevention and/or treatment of sepsis by antibody.

Figure 13:
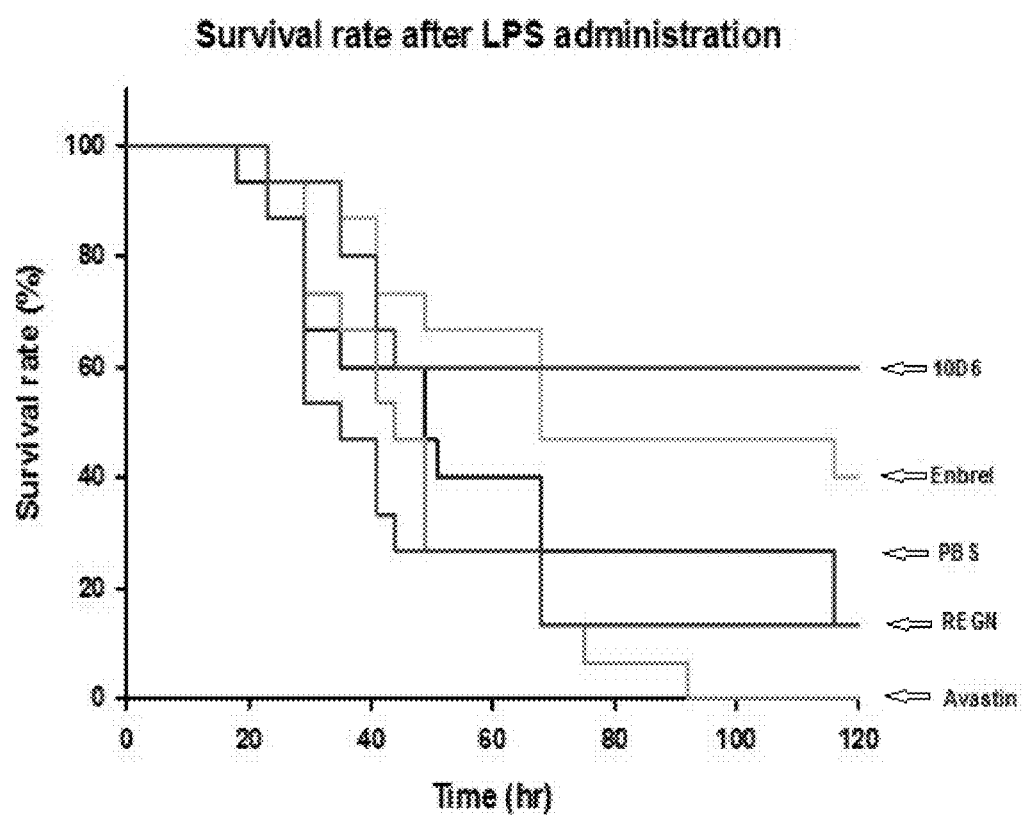
FIG. 13 is a graph showing survival rate of LPS administration-induced sepsis animal models when treated with an anti-Ang2 antibody.

The obtained results are demonstrated in FIG. 13. FIG. 13 is a graph showing survival rate of mice as "%". As shown in FIG. 13, the group treated with antibody 10D6 shows considerable increase in survival rate compared to all comparative groups including control. In particular, at 120 hours, the survival rate of control is 13.3%, the survival rates of comparative groups are less than 40%, whereas the survival rate of 10D6 treated group is about 60%. These results indicate the excellent therapeutic effect of anti-Ang2 antibody according to the present invention in treatment of sepsis.

EXAMPLE 15

Effects of Increase of Survival Rate, Inhibition of Vascular Leakage and Anti-Inflammation by Antibody 10D6 in CLP (Cecal Ligation Puncture) Sepsis Animal Model In order to confirm the effect of antibody 10D6 in other sepsis animal model than LPS-induced sepsis animal model, the effects of antibody 10D6 on survival rate, vascular leakage, and inflammatory response in CLP models, where cecum was tied up and drilled thereby releasing bacteria into abdominal cavity to induce sepsis.

For the experiment, adult C57BL/6 mice (Jackson Laboratory, 6~8 weeks, male) were used. Antibody 10D6 (experimental group), antibody of Regeneron (REGN) (for comparison), COMP-Ang1 (Cartilage oligomeric matrix protein-angiopoietin 1; Tie2 receptor activating substance; Genexel) (for comparison), and 0.5% BSA (control) were intraperitoneally injected at the amount of 10 mg/kg, respectively. After 30 minutes from injection, the mice were anesthetized, and sepsis was induced by tying 75% length of cecum with thread. The survival rates were recorded for 80 hours for confirming the prevention and/or treatment effect on sepsis.

Figure 14:
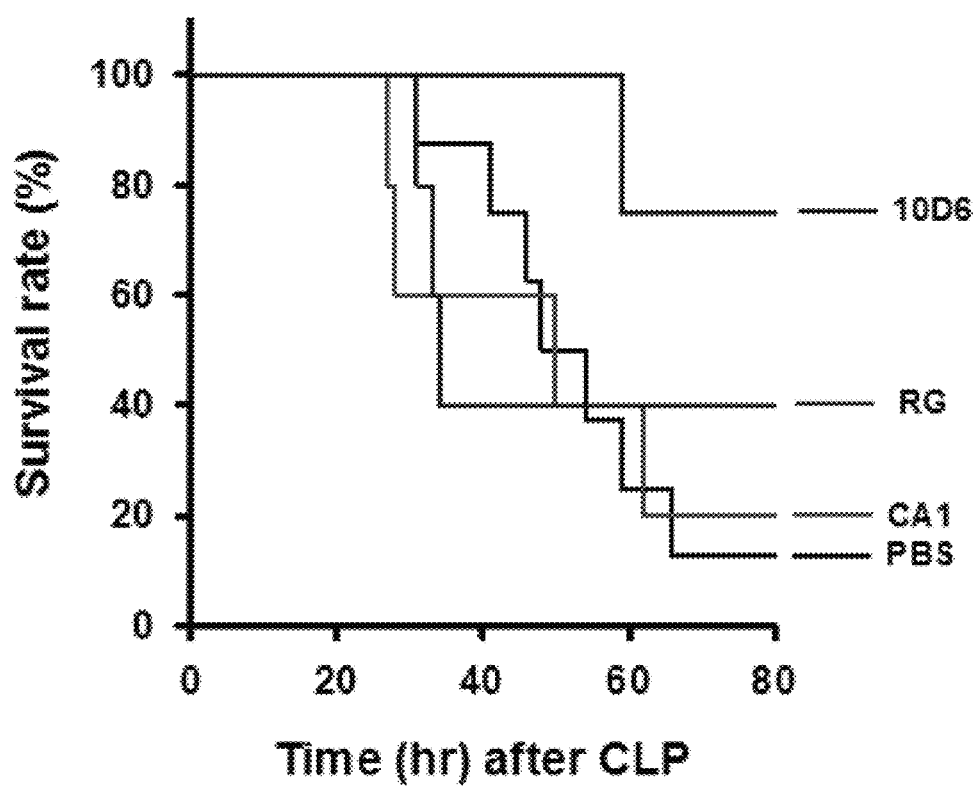
FIG. 14 is a graph showing survival rate of CLP administration-induced sepsis animal models when treated with an anti-Ang2 antibody.

The obtained results are demonstrated in FIG. 14. FIG. 14 is a graph representing the survival rate of mice as "%". Shown in FIG. 14, the survival rate of antibody 10D6-treated group is considerably increased compared to that of comparative groups and control.

In order to confirm vascular leakage inhibition effect and anti-inflammation effect of antibody 10D6, 16 hours after inducing sepsis, lung tissue was removed from each group and analyzed by H&E staining (Hematoxilin and Eosin, DAKO).

Figure 15:
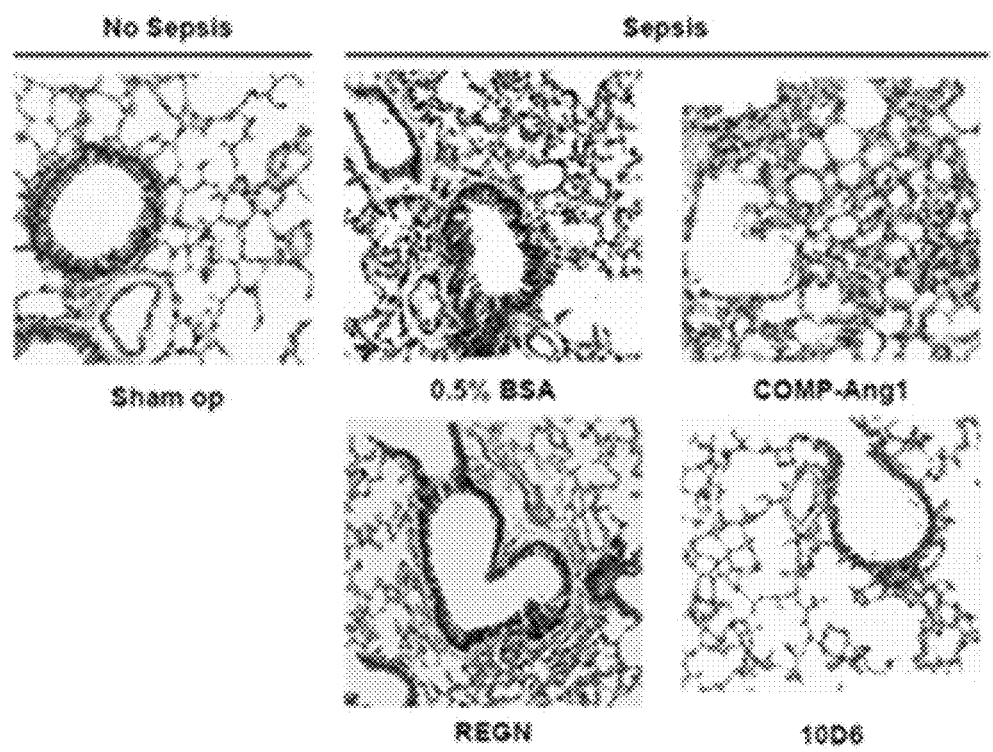
FIG. 15 includes images of lung tissue of CLP administration-induced sepsis animal model, which shows an inhibition of vascular leakage by an anti-Ang2 antibody.

The obtained results are demonstrated in FIG. 15. As shown in FIG. 15, in the lung tissue from sepsis induced mouse, abnormal structure of alveoli and alveolar edema caused by vascular leakage and increase of the number of inflammatory cells are observed. Differently from control and comparative groups, in the antibody 10D6-treated group, the lung tissue maintains its normal structure.

In order to measure the level of inflammation of lung, immunostaining was performed as follows. Frozen sections of lung tissue was blocked with 0.3% TBST (where TBS is mixed with 0.3% Triton X-100) buffer including 5% goat serum (Jackson Immunoresearch) for one hour. Anti-ICAM antibody (rabbit, BD bioscience) and DAPI (Molecular Probe) were added to blocking buffer, and then, the frozen sections were added thereto and allowed to reacting for 3 hours. The obtained reacted result was washed with TBS three times, and then, the mixture of blocking buffer and FITC-conjugated anti-rabbit IgG antibody (Jackson Immunoresearch) was added to the frozen sections to allow to reacting for 2 hours. The obtained sections were washed with TBS three times and covered with coverslip (Marenfield) using Fluorescence mounting medium (DAKO). The stained sections were observed using LSM5 (Zeiss) confocal microscope.

Figure 16:
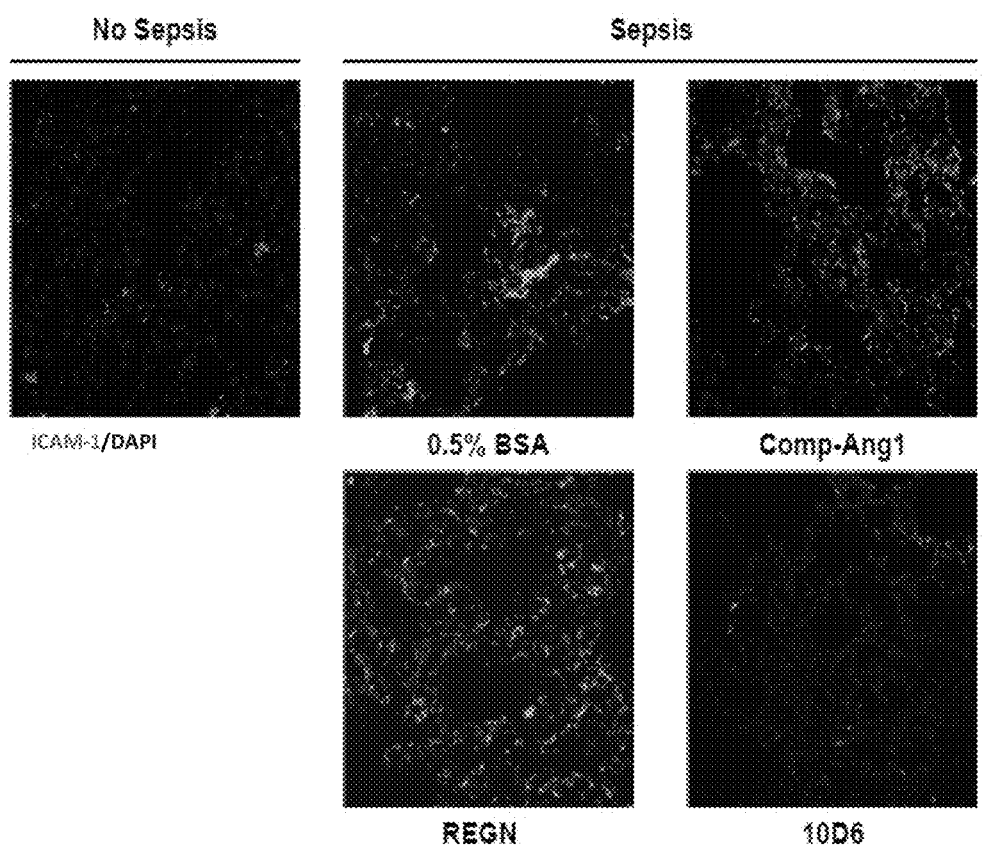
FIG. 16 includes images of lung tissue of CLP administration-induced sepsis animal model, which shows an inhibition of vascular inflammation by an anti-Ang2 antibody.

The obtained results are demonstrated in FIG. 16. As shown in FIG. 16, the expression of ICAM-1 (inflammatory adhesion substance) which is increased by inducing sepsis is decreased to the level of normal lung tissue in the antibody 10D6-treated group only.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of suppressing vascular leakage or vascular inflammation, comprising administering an anti-Ang2 antibody or an antigen-binding fragment thereof to a subject in need thereof, wherein the anti-Ang2 antibody or antigen-binding fragment thereof comprises a polypeptide (CDR-H1) comprising the amino acid sequence of SEQ ID NO: 1, a polypeptide (CDR-H2) comprising the amino acid sequence of SEQ ID NO: 2, a polypeptide (CDR-H3) comprising the amino acid sequence of SEQ ID NO: 3, a polypeptide (CDR-L1) comprising the amino acid sequence of SEQ ID NO: 4, a polypeptide (CDR-L2) comprising the amino acid sequence of SEQ ID NO: 5, and a polypeptide (CDR-L3) comprising the amino acid sequence of SEQ ID NO: 6.

2. The method of claim 1, wherein the subject has vascular leak syndrome, acute respiratory distress syndrome, acute lung injury, or diabetic vascular complication.

3. The method of claim 1, wherein the subject has a vascular infection.

4. The method of claim 1, wherein the anti-Ang2 antibody or an antigen-binding fragment thereof increases the activity of Tie2 by increasing phosphorylation of Tie2 receptor.

5. The method of claim 1, wherein the anti-Ang2 antibody or an antigen-binding fragment thereof increases phosphorylation of at least one selected from the group consisting of Akt, eNOS, and MAPK1 42/44.

6. The method of claim 1, wherein the anti-Ang2 antibody or an antigen-binding fragment thereof comprises a heavy chain variable region including the amino acid sequence of SEQ ID NO: 7 and a light chain variable region including the amino acid sequence of SEQ ID NO: 9.

7. The method of claim 1, wherein the anti-Ang2 antibody or an antigen-binding fragment thereof is produced from a hybridoma deposited with accession number KCLRF-BP-00295.

8. The method of claim 1, further comprising administering Ang2 to the subject.

9. A method of treating sepsis characterized by vascular leakage or vascular inflammation, comprising administering an anti-Ang2 antibody or an antigen-binding fragment thereof to a subject in need thereof comprising administering an anti-Ang2 antibody or an antigen-binding fragment thereof to a subject in need thereof, wherein the anti-Ang2 antibody or antigen-binding fragment thereof comprises a polypeptide (CDR-H1) comprising the amino acid sequence of SEQ ID NO: 1, a polypeptide (CDR-H2) comprising the amino acid sequence of SEQ ID NO: 2, a polypeptide (CDR-H3) comprising the amino acid sequence of SEQ ID NO: 3, a polypeptide (CDR-L1) comprising the amino acid sequence of SEQ ID NO: 4, a polypeptide (CDR-L2) comprising the amino acid sequence of SEQ ID NO: 5, and a polypeptide (CDR-L3) comprising the amino acid sequence of SEQ ID NO: 6.

10. The method of claim 9, wherein the anti-Ang2 antibody or an antigen-binding fragment thereof increases phosphorylation of at least one selected from the group consisting of Akt, eNOS, and MAPK1 42/44.

11. The method of claim 9, wherein the anti-Ang2 antibody or an antigen-binding fragment thereof comprises a heavy chain variable region including the amino acid sequence of SEQ ID NO: 7 and a light chain variable region including the amino acid sequence of SEQ ID NO: 9.

12. The method of claim 9, wherein the anti-Ang2 antibody or an antigen-binding fragment thereof is produced from a hybridoma deposited with accession number KCLRF-BP-00295.

13. The method of claim 9, further comprising administering Ang2 to the subject.

* * * * *